United States Patent [19]

Guo et al.

[11] Patent Number: 4,839,175

[45] Date of Patent: * Jun. 13, 1989

[54] LIPOSOMES WITH ENHANCED RETENTION ON MUCOSAL TISSUE

[75] Inventors: Luke S. S. Guo, Lafayette; Carl T. Redemann, Walnut Creek; Ramachandran Radhakrishnan, Palo Alto; Annie Yau-Young, Los Altos, all of Calif.

[73] Assignee: Liposome Technology, Inc., Menlo Park, Calif.

[*] Notice: The portion of the term of this patent subsequent to Feb. 14, 2006 has been disclaimed.

[21] Appl. No.: 890,815

[22] Filed: Jul. 28, 1986

[51] Int. Cl.$^4$ .................. A61K 37/22; A61K 9/66; B01J 13/02

[52] U.S. Cl. .................. 424/450; 264/4.3; 424/1.1; 424/427; 424/428; 428/402.2; 436/829; 514/912; 514/914; 514/966

[58] Field of Search .................. 428/402.2; 424/450; 436/829; 514/912, 914, 966

[56] References Cited

U.S. PATENT DOCUMENTS

| | | | |
|---|---|---|---|
| 4,229,360 | 10/1980 | Schneider et al. | 424/450 X |
| 4,350,676 | 9/1982 | Laties et al. | 424/9 X |
| 4,480,041 | 10/1984 | Myles et al. | 436/829 X |
| 4,515,736 | 5/1985 | Deamer | 424/450 X |
| 4,544,545 | 10/1985 | Ryan et al. | 424/450 X |
| 4,619,913 | 10/1986 | Luck et al. | 514/2 |

OTHER PUBLICATIONS

M. S. Wu, J. C. Robbins, R. L. Bugianesi et al. titled: Modified in vivo Behavior of Liposomes Containing Synthetic Glycolipids, Bio. Biophysica Acta, 674, (1981), 19–29, Elsevier North–Holland Biomedical Press.

Toshiyuki Nagata, Hansjorg Eibl and Georg Melchers, Fusion of Plant Protoplasts Induced by a Positively Charged Synthetic Phospholipid, pp. 460–462, 0341–0382/79/0500–0460 $01.00/0.

M. M. Ponpipom, T. Y. Shen, J. D. Baldeschwieler, and Po-Shun Wu, titled: Modification of Liposome Surface Properties by Synthetic Glycolipids, (Chapter 7), vol. III, pp. 95–115, Lipsome Technology.

M. R. Mauk, R. C. Gamble and J. D. Baldeschwieler, Titled: Targeting of Lipid Vesicles: Specificity of Carbohydrate Receptor Analogues for Leukocytes in Mice. Prc.: Natl. Acad. Sci. U.S.A., vol. 77, No. 8, pp. 4430–4434, Aug. 1980, Biochemistry.

H. E. Schaeffer and D. L. Krohn. Titled: Liposomes in Topical Drug Delivery, pp. 220–227, Invest. Ophthalmol. Vis. Sci., Feb. 1982, 0146–0404/82/020220.

*Primary Examiner*—Richard D. Lovering
*Attorney, Agent, or Firm*—Peter J. Dehlinger

[57] ABSTRACT

A liposome composition designed for enhanced binding to mucosal tissue, The liposomes contain about 10–40 mole percent of an amine-derivatized lipid component in which a charged amine group is spaced from a lipid polar head region by a carbon-containing spacer arm at least 3 atoms in length. The liposomes preferably have a close packed lipid structure produced by inclusion of between 20–50 mole percent of cholesterol or an amine-derivatized cholesterol, and/or phospholipids with predominantly saturated acyl chain moieties. For ophthalmic use, the liposomes may be suspended in an aqueous medium containing a high-viscosity polymer, to enhance further the retention of liposomes on a corneal surface.

10 Claims, 2 Drawing Sheets

LIPOSOMES WITH ENHANCED RETENTION ON MUCOSAL TISSUE

FIELD OF THE INVENTION

The present inventioin relates to liposomes designed for enhanced binding to mucosal tissue, and to a drug delivery system and method which uses the liposomes.

REFERENCES

Anderson, R.L., et al, Invest. Dermatol. 58:369 (1972).
Chabala, J.C., et al, Carbohydr Res 67:55 (1978).
Doebbert, T.W., et al, J Biol Chem 257(5):2193 )1982).
Doody, M.C., et al, Biochemistry 19:108 (1980).
Heath, T.D., et al, Biochim Biophys Acta 640:66 (1981).
Huang, C.H., et al, Lipids 12:348 (1977).
Kantor, H.L., et al, Biochemistry 17:3592 (1978).
Lawrence, D.J., et al, Ann NY Acad Sci 106:646 (1963).
Lee, V.H.L., et al, Survey of Ophthalmol 29:335 (1985).
Lemp, M.A. et al. Int Ophthalmol Clin 13:185 (1973).
Massari, S., et al. Biochim Biophys Acta 599:188(1980).
Mauk, M.R., et al, Proc Nat Acad Sci USA 77 (8):4430 (1980 )
Nagata, T.et al. Z. Natureforsch 34c:460 (1979).
Papahadjopoulos, D., et al, Biochim Biophys Acta 330:8 (1973).
Papahadjopoulos, D., et al, Biochim Biophys Acta 448:254 (1976).
Ponpipom, M.M., et al, Can J Chem 58:214 (1980).
Ponpipom, M.M. et al, J Med Chem 24:1388 (1980).
Ponipipom, M.M., et al. in *Liposome Technology*, Vol III, pp 95-115 (1984).
Robbins, J.C., et al, Proc. Nat Acad Sci USA 78(12):7294 (1981).
Schaeffer, H.E., Invest Ophthalmol Vis Sci 21:220-227 (1982).
Sjögren, H., et al, Sury Ophthalmol 16:145 (1971).
Szoka, F., Jr., et al. Ann Rev Biophys Bioeng 9:467 (1890).
Wu, M.S., et al, Biochim Biophys Acta 674:19 (1981 ).
Wu, P.S., et al, Proc Nat Acad Sci USA 78(4):2033 (1981).
Yashihara, E., et al, Biochim Biophys Acta 854:93 (1986).

BACKGROUND

Mucosal body surfaces, such as the corneal surface, and the surface epithelial lining of body cavities, are potentially useful sites for drug administration. For example, many ophthalmic diseases, such as viral and bacterial infections, and chronic conditions, such as glaucoma, can be treated by topical durg administration to the ocular surface. Other mucosal tissue sites. including the nose. mouth, throat. rectum, vagina, and stomach are also important target areas of direct drug adiministration.

Currently, many ophthalmic drugs are applied in soulution form to the ocular surface. A majon problem with this approach is limited drug uptake, since the drugs solution is rather quickly washed away by tearing action. Because of the rapid clearance, an ophthalmic drugs may have to be adiministered several times a day. The frequent doses which are needed reduce patient compliance, and can be quite uncomfortable for the patient, as in the case of common anti-glaucoma drugs which cause blurred vision for several hours after application.

The retention of a solution-form drugs on the corneal surface can be enhanced by the use of polymers. such as hydroxythylcellulose or methylcellulose, which increase the viscosity of the drug solution. Polymer containing viscous liquids are used, for example, in the treatment of dry eye, to help keep the corneal surface moist. However, with the increased viscosity, very little of the originally applied liquid is retained for more than about an hour, so frequent dosing is necessary.

For body-cavity sites, suppositories are a convenient method for releasing medication to the mucosal tissue over an extended period, and for drug release in the stomach, slow release particles that break down at variable rates are commonly used. Even though suppositories and slow-release particles may give sustained drug release in the region of the mucosa, only a small percentage of the release drug may be taken up by the mucosa, due to rapid drug "clearance" by the normal cavity fluids.

The concept of using liposomes to enhance the delivery of drugs at a mucosal tissue has been proposed, but this approach has been limited heretofore by relatively poor retention of liposomes on mucosal tissue (Lee). Studies conducted in support of the present invention, for example, show that retention of conventional liposomes on an ocular surface is less than about 5% after 1 hour. Thus, even though liposomes have the capability of controlled drug release over a several hour period, this feature has not been exploitable in the past bacause of poor liposome retention at the target site.

Some improvement in liposome retention has been reported for liposome containing charged lipids, such as cholesteryl amine, into liposome. Presumably the increased retention is due to the interaction of the liposome surface positive charges with mucin, a negatively charged glycoprotein which is secreted by and present in the environment of mucosal tissue. Ocular-retention studies performed in support of the present invention show that at a cholesterol amine concentration of 40 mole percent, liposome retention at the end of an hour increases from about 5% for uncharged liposomes to about 10% of the originally applied liposomes. This small increase in enhancement falls short of the increase in liposome retention which would be needed to provide effective drug release several hours after the liposome are applied to the mucosal surface.

Relatively long chain alkyl amines, such as stearylamine, have been used to increase retention of liposomes to ocular mucosa (Schaeffer). However, charged amines of this type tend to be toxic at elevated levels (Yashihare) and therefore cannot be used at molar concentrations that give maximal liposome retention properties. This problem is aggravated in part because the single chain molecules of this type can readily dissociate from the liposome bilayer, and because the molecules themselves tend to destabilize the liposome bilayer structure.

BACKGROUND OF THE INVENTION

It is therefore a general object of the invention to provide, for administering a drug to a mucosal tissue site, a drug/liposome composition which has significantly enhanced retention on mucosal tissue.

A more specific object is to provide such a composition for use in administering drugs to the eye, at a controlled drug-release rate of over several hours.

Still another object of the invention is to provide an improved liposome composition for the treatment of dry eye.

It is yet another object of the invention to provide, for formulation into one of a number of possible liposome vehicles, a drug/liposome composition having an enhanced binding affinity for mucosal tissue.

According to one aspect of the invention, it has been discovered that significantly enhanced liposome binding to mucosal tissue is achieved if the outer surfaces of the liposomes contain positive surface charges which are (a) anchored to the lipid outer lipid bilayer structure by vesicle-forming lipids which are relatively tightly associated with the membrane, and (b) spaced by at least about a 3 atom spacer from the polar head regions of such vesicle-forming lipids. The concentration of surface positive charges is typically between about 20-50 mole percent. In addition to the spacing of positive charges from the liposome surfaces, relatively tight packing in the bilayer membrane has been found to contribute to the enhancement of liposome retention on mucosal tissue. This packing effect can be achieved either by the presence of cholesterol or a cholesterol derivative, at a concentration of between about 20-50 mole percent, or by the use of phospholipid or diglyceride components containing predominantly saturated acyl chain moieties. The positive charges can be derivatized to either phospholipid or cholesterol components forming the vesicles.

More specifically, the invention includes a liposome composition in which the liposomes have outer lipid bilayer surfaces containing (a) between about 40-80 mole percent of neutral vesicle forming lipid components, and (b) between about 20-60 mole percent of positively-charged vesicle-forming lipid component(s) having (i) 2 aliphatic chains carried on a 3-4 carbon backbone, (ii) a polar atom attached to the backbone at a carbon atom which does not carry an aliphatic chain, (iii) an amine linked to the polar atom through a spacer at least 3 atoms long, and (iv) a net positive charge. The liposomes may also include a cholesterol derivative having an amine group linked to the A ring 3 position by a spacer arm at least three atoms long.

The liposome preferably have a relatively close-packed lipid structure by virtue of containing between about 20-50 mole percent cholesterol or cholesterol analog or amine derivative, and/or predominantly saturated acyl chain moieties in the phospholipid or diglyceride components.

One preferred positively charged lipid component is an amine-derivatized phospholipid of the form:

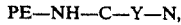

PE—NH—C—Y—N, where PE—NH$_2$ is phosphatidylethanolamine, and Y is a basic amino acid or peptide containing a basic amino acid. The derivated PE is formed by coupling PE with the anhydried of the amino acid or peptide.

One preferred cholesterol derivative has the form

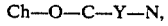

Ch—O—C—Y—N, where Ch—OH is cholesterol, and Y is a carbon-containing chain at least 2 atoms in length. The lipid component is formed by coupling cholesterol with the anhydride of an amino acid or peptide.

Another preferred cholesterol derivative has the form:

Ch—NH—Y—N, where Ch—NH is cholesterol-3-aine and Y is a carbon-containing chain at least 2 atoms in length. The component is formed by coupling a diamine with a cholesteryl-3-halide.

The liposome composition may further be formulated for increase retention near the tissue site (as well as increased retention to the mucosal tissue). For ophthalmic uses, the formulation may include increase-viscosity polymers. For uses in body cavities, the liposome may be formulated for delayed release in suppositories or slow-release polymer matrices. Aerosolized liposomes for nasal and oral drug deliverly, and cream or foam formulations for topical application are also disclosed.

Also forming part of the invention is an improved method of administering a drug to a mucosal tissue, for sustained drug release at the tissue site over a several hour period. The method utilizes the novel liposome composition described above.

In still another aspect, the invention includes a method of treating dry-eye, by applying to the ocular surface, a preferably optically clear suspension of positively charged liposomes of the type described above. The suspension may contain increased-viscosity polymers for greater liposome retention at the ocular site. The liposomal lipids contribute to the lubricating properties of the dry-eye composition.

These and other object and features of the invention will become more fully apparent when the following detailed description of the invention is read in conjunction with the accompanying drawings.

Figure 6:
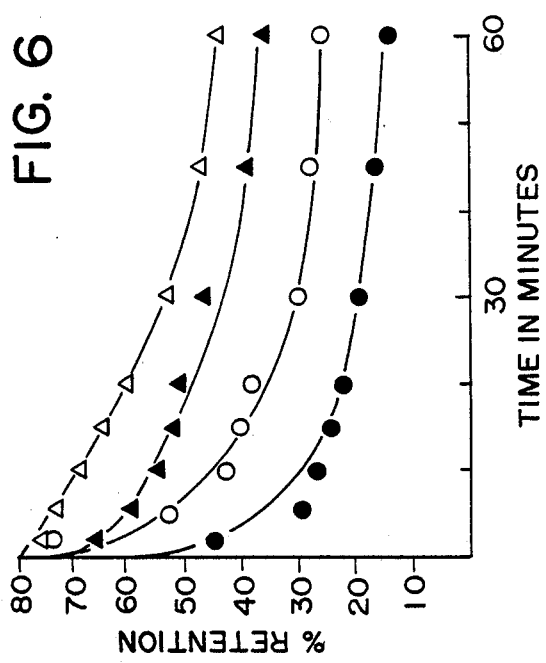
Figure 7:
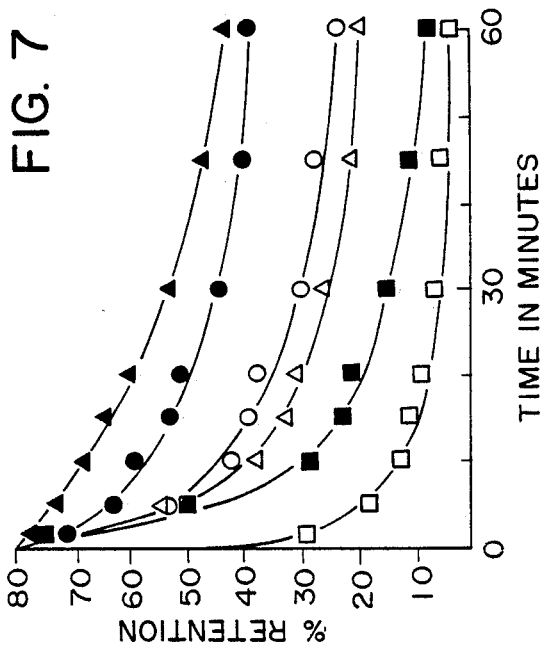

FIG. 6 shows the retention on an ocular tissue of liposomes prepared with either lysine PE (circles) or lysine lysinyl PE (triangles), in a suspension containing either buffer (closed symbols) or polymers (open symbols): and FIG. 7 shows the retention on an ocular tissue of liposomes prepared with either lysinyl PE, at 20 (open circles) or 30 (closed circles) mole percent, or lysine lysinyl PE, at 10 (open triangles) or 20 (closed triangles) mole percent, in a suspension containing a polymer additive, and neutral liposomes with (closed squares) or without polymer additive (open squares).

DETAILED DESCRIPTION OF THE INVENTION

I. Preparing Amine-Derivatized Lipid Components

A. Structural Requirement

The positively charged lipid components used in preparing the liposomes of the invention are characterized by: (i) 2 aliphatic chains carried on a 3-4 carbon backbone, (ii) a polar atom attached to the backbone at a carbon atom which does not carry an aliphatic chain, (iii) an amine linked to the polar atom through a spacer at least about 3 atoms long, and (iv) a net positive charge. Exemplary lipid components include diglycerides, and amine analogues thereof, in which the polar atom is a hydroxyl oxygen or amine, respectively; glycolipids, in which the polar atom is the acetal oxygen joining the suger residue to the lipid backbone; and phospholipids, in which the polar atom is a phosphate ester oxygen linking a glycerol backbone to a phosphate polar head group. In all of these lipid types, the polar atom is positioned on the outer bilayer surface of the lipid vesicles at a position corresponding approximately to the hydroxyl group of cholesterol. The liposomes may also contain positively-charged cholesterol derivatives having an amine group linked to the 6-membered cholesterol A ring by a carbon-containing chain at least 3 atoms in length.

Both the dialiphatic chain lipids and cholesterol are relatively tightly associated with liposome bilayer structure, and contribute to membrane stability. These properties are in contrast to single acyl chain compounds, such as fatty acids or their derivatives, which readily dissociate from membrane bilayer structures in an aqueous suspension (Doody), and which also promote fusion of lipid bilayers (Kantor) and stimulate phospholipid release (Massari) and intermembrane lipid exchange (Papahadjopoulos). Another distinguishing feature of dialiphatic and cholesterol lipids, when compared with single acyl chain components, is their more rigid radial positioning in the lipid planes of the bilayer structure.

According to an important aspect of the invention, it has been found that good enhancement of liposome retention requires that the positively charged amine groups be spaced from the polar head region of the lipid by at a carbon-containing spacer arm at least three atoms long. This spacer is apparently needed to allow the lipid-bound amine groups to interact readily with negatively charged molecules in the mucosal surface environment. Evidence for the three-atom spacer requirement comes from a number of studies on the binding of liposomes to ocular and other mucosal tissues which were carried out in support of the invention. Two of these studies, reported in Example X, examine the effect of cholesteryl amines and cholesterol amine ester having various selected spacer chain lengths. The data on cholesteryl amines is summarized in FIG. 3, which shows that liposomes containing epi-cholesteryl amine (open circles) are comparable to uncharged liposome (closed squares) in liposome retention. By contrast, a epi-cholesteryl piperazine derivative, with a several atom chain (open triangle), shows about 50% retention after 1 hour.

A more systematic study on chain length, also reported in Example X, compares the ocular retention of liposome containing 40 mole percent of the cholesterol ester of glycine (open circles), $\beta$-alanine (open squares) and $\epsilon$-aminocaproic acid (closed triangles). As seen in the FIG. 4, the glycine derivative, in which the amine is spaced from the cholesterol hydroxyl oxygen atom by only two carbon atoms, gives only a slight enhancement over control liposome containing underivatized cholesterol (closed squares). By contrast the cholesterol derivatives of both $\beta$-alanine (three carbon spacer) and $\epsilon$-aminocaproic acid (6 carbon spacer) gave a severalfold increase in binding retention after 1 hour.

The spacer chain is a carbon-containing chain having various degrees of saturation and/or heteroatom compositions. One preferred type of chain is a simple saturated acyl chain. The carbon atoms in the chain may also be partially unsaturated, including either ethylenic or ethynic bonds, and/or may include such heteroatoms as carbon-linked oxygen (O), sulfur (S) or nitrogen (N) atoms, forming ester, ether, thioester, thioether, amide or amine linkages within the chain. The chain atoms themselves may be substituted with carbon, hydrogen, O, S, or N atoms, or groups containing these atoms such as short chain acyl groups or the like. Further, the chain may contain a glycoside group which carries the amine, and is itself attached to lipid backbone through a suitable spacer arm.

The positively charged amine may be either a primary, secondary, tertiary, or quaternary amine, with the only requirement that the amine be positively charged at the operative pH. In general primary, secondary, and tertiary amine are positively charged at a pH below about 7.5-10. One advantage of quaternary amines is that the species is always positively charged, independent of pH.

Structural features and methods of synthesis of selected positively charged lipid components will now be considered.

. Dialiphatic Lipid Derivatives

As defined herein, the term dialiphatic lipid is intended to include amphipatic lipids having (i) a 3-4 carbon backbone, (ii) two aliphatic chains carried on the backbone, and (iii) a polar oxygen or nitrogen atom attached to a backbone carbon atom which itself does not carry an aliphatic chain. The aliphatic chains are attached to the backbone by suitably stable linkage, including acyl ester, ether, thioether, amine, carbamate, or a dioxolane ring (Nagata) linkages. As indicated above, exemplary dialiphatic lipids include diglycerides and phospholipids, in which the aliphatic chain are fatty acyl chains attached to a glycerol backbone through acyl linkages and glycolipids, in which one of the acyl chains may be linked to the backbone through an amide linkage.

The aliphatic chains in the lipid components are preferably at least about 12 atoms in length, and optimally between about 15-20 atoms long. The chains are also preferably substantially unsaturated, by which is meant that each chain contains at most one unsaturated bond, and preferably an ethylenic bond. The substantially unsaturated aliphatic chains produce better lipid packing in the liposomes, which has been found to increase liposome binding to mucosal surfaces. In addition, the more unsaturated chains produce greater chemical stability on ling term storage, and evidenced by reduced oxidative damage to the lipids.

In derivatized form, diglyceride and diglyceride amine analogues contain an amine attached to the polar oxygen or nitrogen atom through a spacer arm at least three atoms long. The diglyceride derivatives may be formed by known coupling methods involving glycerol hydroxyl or amine groups. In general, these methods are similar to used in derivatizing cholesterol or cholesteryl amine, as described below. For example, the diglyceride can be reacted with a protected amino acid anhydride, according to above-described methods, to form the diglyceride ester of the amino acid.

As defined herein, the term phospholipids encompasses phosphatidic acid (PA) and phosphatidyl glycerol (PG), phosphatidylcholine (PC), phosphatidylethanolamine (PE), phosphatidylinositol (PI), Phosphatidylserine (PS), plasmalogens, and sphingomyelin (SM).

The polar end region of the phospholipids is defined as the glycerol hydroxy oxygen atom which forms the glycerol/phosphate ester linkage in the phospholipid. This oxygen atom occupies roughly the same radial position in a lipid bilayer surface as the hydroxy oxygen atom in diglycerides, and therefore about the same radial position as the 3-hydroxy oxygen atom in cholesterol.

The phospholipid derivatives (other than PA derivatives) differ from the above cholesterol and diglyceride derivatives in that the polar end region hydroxy oxygen is itself linked, through a phosphate ester bond, to a carbon containing chain at least three atom long, i.e., the phosphate-ester linked moiety defining the individual class of the phospholipid. Thus it is only necessary, in forming the positively charged phospholipid (other than PA) for use in the invention, to place a net positive charge at or near the end of the phosphate-ester linked moiety in the phospholipid. Several phospholipids, including PC, and PE, contain chain terminal amines which in the natural phospholipid, balance the negative charge of the phosphate group. These phospholipids can be converted to the desired positively charged derivatives by acylating the phosphate group, thus neutralizing its charge and imparting a net positive charge (due to the terminal amine) to the derivative. Methods for methylating or ethylating ester-linking phosphate groups, to form corresponding methylphosphonate or ethylphosphonate derivatives are known, and would be suitable for use in the present application.

In another general approach, the phospholipid is derivated by coupling an amine, such as an amino acid, to a reactive end group in the phosphate-ester linked moiety of the lipid. A variety of coupling reactions involving suitable activating agents or reactive species are known, and can be readily adapted for coupling amines to natural phospholipids. For example, PE and plasmalogens can be coupled through the terminal primary amine to an amine via an amide linkage, according to known coupling reactions, as will be detailed below. PI and a variety of glycolipids, which contain a terminal glycoside group, can be coupled to an amine after a prior periodate reaction (Heath) which involves initial aldehyde formation, and proceeds through a Schiff base. PS can be coupled through its terminal acid group, by known amide-forming reactions to suitable amines. It is noted here that the amine coupled to PA must serve to extend the charged amine at least 3 atoms from the phosphate-ester linked oxygen attached to the lipid's glycerol moiety.

The amine which is coupled to the phospholipid has a total number of charged amine groups which will impart a net positive charge of at least 1 to the derivatized phospholipid. Thus, where the amine is joined to PE or a plasmalogen through an amide linkage, the amine must contain at least two amine groups—one to balance the phosphate negative charge, to offset the loss of the terminal amine charge in the phospholipid, and a second to contribute a single net positive charge. Preferred double amines for use in derivatizing PE are basic amino acids such as lysine, ornithine, histidine, or arginine, or peptides containing at least one such amino acid. As a further illustration, in derivatizing PS through an amide linkage involving the terminal acid group, a diamine would also be required—one amine to react with the acid group, and a second amine to contribute a single net positive charge. The following methods for forming amine-derivatized PE are exemplary.

Purified or partially purified PE used in preparing the cationic PE derivative is commercially available, or may by prepared by known methods. The lipid may be purified and/or modified in acyl chain composition according to known techniques. In certain liposome formuations and applications, to be discussed below, it is desirable to employ PE components having predominantly saturated acyl moieties; for other applications more unsaturated lipid components may be preferred.

One method for forming the amine derivatized PE component is illustrated in Example I for the preparation of lysinyl and lysine lysinyl PE, and in Example II, for the preparation of arginyl PE. As a first step, the basic amino acid or peptide is N-protected, such as by reaction with di-t-butyldicarbonate. The protected amino acid is then reacted with an approximately equimolar amount of a condensing agent, such as dicyclocarbodiimide (DCC), to form the anhydride of the protected amino acid. The reaction conditions described in Example I are generally suitable in the anhydride-forming reaction. The anhydride may be used further without removing the dicyclohexylurea which forms as a by-product of the reaction. The anhydride in now reacted with PE under anhydrous conditions, to couple the protected amino acid to the PE through an amide linkage. The reaction product is deprotected, such as by treatment with trifluoroacetic acid, and may be purified, by chromatography on silica gel. The eluate fractions can be monitored conventionally by thin-layer chromatography (TLC), as described in Example I and II. The purified product may be stored as a dry residue under nitrogen at 4° C. for up to several months.

In a second method for forming the amine PE derivative, the protected amine is reacted directly with an N-hydroxysuccinimide in the presence of DCC to form the corresponding N-hydroxysuccinimide ester of the amino acid. Typical reaction conditions are similar to those used in forming the amino acid anhydride. The material may be employed without further purification for reaction with PE. The reaction product is deprotected and purified as above, and as detailed in Example I.

C. Cholesterol Derivatives

As defined herein, the term cholesterol is intended to encompass cholesterol, (3-hydroxy-5,6-cholestene), and related analogs, such as 3-amino-5,6-cholestene, and 5,6-cholestene and cholestane and related analogs, such as 3-hydroxy-cholestane. The polar end region of cholesterol is defined as the polar atom, such as oxygen or nitrogen, which is directly attached to the 3 position of the 6-membered A ring of the cyclopentanoperhydrophenanthrene nucleus of cholesterol, according to conventional ring and ring position identification. The amine-derivatized cholesterol has the general formula: Ch—O—X—N or Ch—NH—X—N, where Ch—O or Ch—N is a cholestene or cholestane structure with a 3 position oxygen or nitrogen, X is a carbon containing chain at least three atoms long, and N is a charged primary, secondary, tertiary, or quaternary amine.

One exemplary cholesterol derivative is a cholesterol ester of the form: Ch—O—C—Y—N, where Ch—OH is 3-hydroxy-5,6-cholestene, and Y is a carbon-containing chain at least two atoms long.

To form the cholesterol ester, an amino acid of the form $CO_2$—Y—N is N-protected, by reaction with di-t-butyldicarbonate, and reacted with a suitable condensing agent, such as DCCI, to form the corresponding anhydride of the protected acid. The anhydride is reacted with an approximately equimolar amount of cholesterol, forming the derivatized, protected compound, which is then deprotected and purified, for example, by silica gel chromatography. Example III illustrates these reaction methods for forming the cholesterol esters of the five amino acids $CO_2(CH_2)_nNH_2$, where $n=1-5$. The reaction conditions are applicable to other amino acids having one or more free amine groups. As noted above, only those cholesterol ester derivatives in which the free amine is spaced from the cholesterol hydroxyl by three or more atoms (n greater than or equal to 2 in the Example III compounds) produce significant binding enhancement of liposomes to mucosal tissue.

It will be appreciated that more than one net positive charge may be derivatized to the cholesterol, either by coupling to a basic amino acid, such as lysine, or by coupling to a peptide containing more than one free amine group.

A second cholesterol derivative is a cholesteryl amine of the form: Ch—NH—X—N, where Ch—NH$_2$ is 3-amino-5,6-cholestene and X and N are as defined as above.

The derivative is formed by reacting a cholesteryl-3-halide, such as cholesteryl-3-iodide with a diamine of the form NH$_2$—Y—N, where N is a primary-quaternary amine, and preferably a primary amine. Typically, about a tenfold molar excess of the diamine is reacted with the cholesteryl halide in a suitable solvent, such as dimethylsulfoxide. The product is extracted into a lipophilic solvent, such as toluene, and may be purified by silica gel column chromatography. Reaction details for the synthesis of (5-cholesten-3-α-N-(-3-(4-(3-aminopropyl)piperazino)propyl)amine) from cholesteryl iodide and N,N"-bis-(3-aminopropyl)-piperazine are given in Example IV. Also described in Example IV is the synthesis of cholesterol-3-amine, which was synthesized as a control compound.

Methods for derivatizing thiocholesterol through a disulfide linkage have also been reported (Huang, Baldeschweiler).

In addition, a variety of cholesterol amine and amino glycoside compounds having the requisite cholesterol/spacer arm/amine structure have been reported. The compounds were prepared, along with a variety of different uncharged thio-linked glycoside cholesterol analogues, to examine the feasibility of targeting liposomes containing a selected surface glycoside to specific tissues, based on liposome interactions with glycoside-specific tissue receptors. (Ponpipom, 1980, 1981, 1984; Chabala; Wu, M; Wu, P.; Robbins; Mauk; and Doebbert). Liposomes incorporating several of these cholesterol derivatives show a variety of glycoside-specific effects, including enhanced uptake by macrophages, increased retention at subcutaneous injection site, increased stability in vivo, and tissue-specific liposome distribution. Comparative studies with a variety of uncharged glycosidic cholesterol derivatives, and with charged, but non-glycosidic cholesterol derivatives, including aminohexylcholesterol, and amino ethyl cholesteryl carbamate, suggest that the pharmocokinetic effects observed are related primarily to glycoside interactions with tissue specific receptors, rather than to non-specific charge interactions, as in the present invention. Where charge-related effects were observed, e.g., in liposome stability in vivo (Mauk), the mole percentage of charged lipid was relatively low (less then ten percent).

II. Liposome Preparation

A. Lipid Components

Figure 2:
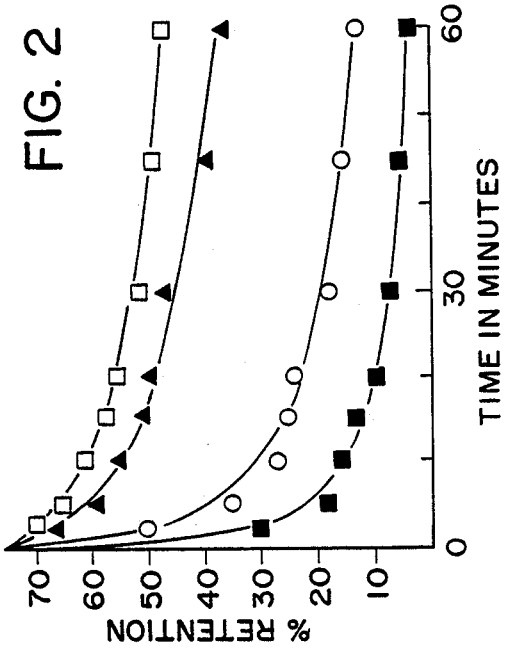
FIG. 2 shows the retention on an ocular tissue of liposomes prepared with increasing concentrations of lysine lysinyl PE, including a neutral lipsome control (solid squares), and 10 (open circles), 20 (closed triangles), and 30 (open squares), mole percent lysine lysinyl PE.
Figure 1:
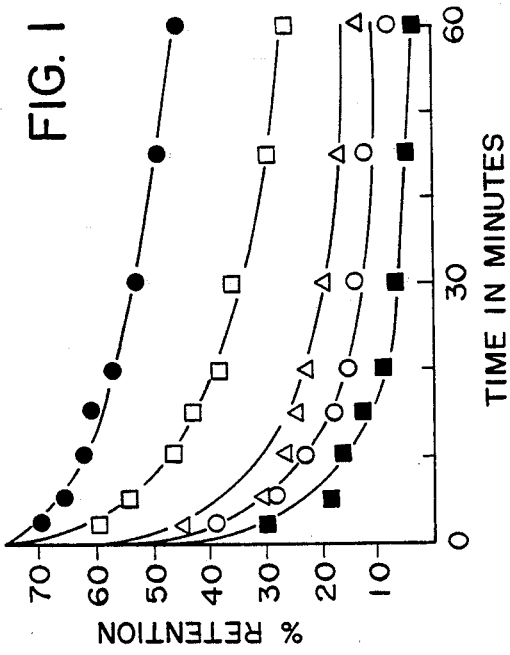
FIG. 1 shows the retention at an ocular tissue of liposomes prepared with increasing concentrations of lysinyl phosphatidylethanolamine, (lysinyl PE), including a neutral liposome control (solid squares), and 10 (open circles), 20 (open triangles), 30 (open squares), and 40 (closed circles) mole percent lysinyl PE.

The liposomes of the invention are formed of a mixture of neutral and amine-derivatized lipids. The neutral lipids, which typically constitute between about 40–80 mole percent of the total liposomal lipids, are predominantly phospholipids, such as PC and Pe, and/or cholesterol or cholesterol analogues. The amine-derivatized lipids preferably make up about 20–60 mole percent of the total lipid components. Studies showing the effect of charge density on lipsome retention are presented in Examples VIII, below, and are shown in FIGS. 1 and 2. FIG. 1 is a plot of ocular retention against time with liposomes containing increasing amounts of lysinyl PE, from 0 to 40 percent. As seen in FIG. 1, liposomes containing no lysinyl PE (solid squares) were retained at less than about 5% after 1 hour. Increasing the amount of lysinyl PE from 10 (open circles), to 20 (open triangles), to 30 (open squares) to 40 (solid circles) mole percent gave progressively enhanced retention, with 40 mole percent liposomes showing nearly 50% retention after 1 hour. FIG. 2 shows the same increased-retention effect, but with increasing mole percentages of lysine lysinyl PE. Here both 20 (solid triangles) and 30 (open circles) mole percent charged lipid gave strong enhancement of ocular retention. Generally, enhancement of binding can be achieved at a concentration of charged lipid between about 20–50 mole percent, although higher mole ratios of the charged lipids are permissible. The charge concentration can be achieved either by about 20 mole percent of a single charged lipid component, such as lysinyl PE, of 10 mole percent of a doubly charged component, such as lysine lysinyl PE, and so on.

The charge concentration noted above apply only to the outermost lipid layer in the liposomes, and therefore the liposomes need not have a uniform charge density through their one or more bilayer regions. In fact, studies conducted in support of the present invention indicated that in small unilamellar vesicles (SUVs), positive charge seems to localize preferentially on the outer of the two lipid layers forming the vesicle bilayer. The study is described in Example VII. As seen there, SUVs formed with 20 mole percent lysinyl PE have contain about 75% of the total positive lipid charge in their outer lipid layer, and SUVs formed with 20 lysine lysinyl PE contain about 92% of the positive lipid charge in the outer layer. This unequal transbilayer distribution of charge is probably related to the greater polar charge repulsion which is present on the inner side of the bilayer. The studies indicate in any case that the requisite 20 mole percent charge distribution on the outer liposome surface can be achieved with less than 20 mole percent actual lipid used in formulating the liposomes.

The liposomes may further include minor amounts of other vesicle-forming lipids, such as fatty acids, negatively charged phospholipids, glycolipids, and the like, with the proviso that these minor lipid components (a) do not significantly reduce the binding affinity of the liposomes for mucosal tissue and (b) are not toxic at the mucosal tissue site. The first prescription limits the amount of negatively charged lipid which can be included in the liposomes, and also the amount of lipid which is disruptive of lipid packing in the liposome bilayer.

In the following discussion, the considerations governing the choice of phospholipid and sterol components generally apply both to neutral and amine-derivatized components, it being recognized that either the phospholipid or cholesterol components or both may contain at least some amine-derivatized species.

Figure 5:
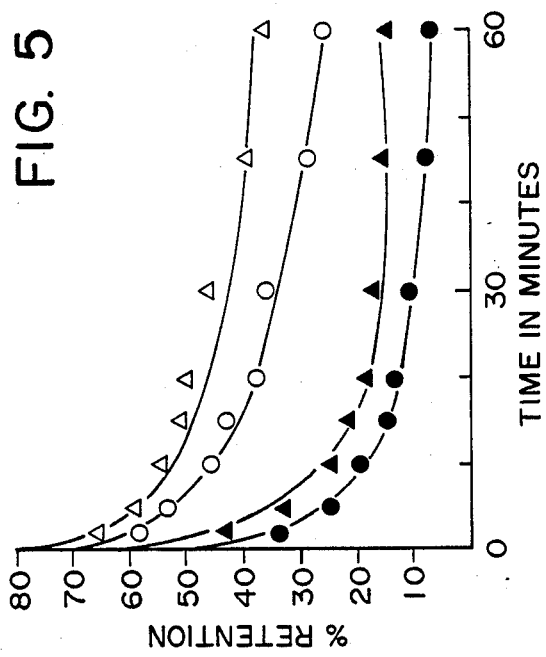
FIG. 5 shows the retention on an ocular tissue of liposomes prepared with either 0 (closed symbols) or 40 (open symbols) mole percent cholesterol, and 20 mole percent of either lysine PE (circles) or lysinyl PE (triangles).

One consideration in the choice of phospholipid components is the degree of saturation of acyl chain moieties. Experiments conducted in support of the invention show that the enhanced liposome retention on mucosal surfaces which is achieved with amine-derivatized lipid components is enhanced still further using lipid components which tend to increase the packing density of lipids in the vesicle bilayers. In particular, a enhanced retention is seen either with addition of cholesterol or a cholesterol derivative, or with a high percentage of saturated phospholipid acyl chain components, both of which are known to increase lipid packing (Papahadjopoulos, 1973). Studies on the effect of cholesterol on lipsome binding to an ocular surface are detailed in Example VIII. With reference to FIG. 5, which summarizes the data, it is seen that the addition of 40 mole percent cholesterol (open symbols) significantly increased the binding affinity of liposomes containing either lysinyl PE (circles) or lysine lysinyl PE (triangles). Cholesterol alone, in the absence of added amine-derivatized PE, produced no appreciable binding enhancement. Similar results were seen in PC/lysine PE liposomes, where PC with saturated acyl chains gave signficantly greater retention of the amine-derivatized liposomes than did egg PC.

The degree of saturation of phospholipid components can also have a major effect on the rate of release of entrapped drug from the liposomes. In general, more saturated lipids prolong the release of entrapped drugs, with a significant increase in release rate being observed near the transition temperature of the lipids. For many drugs, the release half life in liposomes with predominantly saturated lipids is several hours to several days, which can mean that over a several-hour period of liposome binding to a mucosal surface, only a small portion of the entrapped drug is actually released from the liposome for uptake by the tissue. The presence of high molar amounts of cholesterol, by contrast, does not effect drug release rates substantially. For this reason, it may be advantageous to achieve close packing in the liposomes by the inclusion of cholesterol rather than saturated phospholipid or diglyceride components.

Still anothe consideration in the choice of the lipid components is extent of lipid oxidative/peroxidative damage which can be tolerated. It is known, and experiments conducted in support of the invention have confirmed, that both unsaturated phopholipids and cholesterol are susceptible to lipid oxidative damage, particularly where the lipids are stored over an extended period at above refrigeration temperatures. The problem of lipid oxidation damage would therefore be quite sever for a lipsome product, such as an ophthalmic eye-drop composition, which is normally sold and stored at room temperature. Reduced oxidation can be achieved by using predominantly saturated lipid components, such as saturated phospholipids and diglycerides and cholestane sterols.

Lipid peroxidative damage can also be reduced by a combination of a lipophilic free radical scavenger, such as $\alpha$-tocopherol ($\alpha$-T), and a water-soluble iron-specific chelator, such as desferrioxamine. This combination of protective agent is discussed in U.S. patent application "Liposome/Anthraquinone Drug Composition and Method", Ser. No. 806,084, filed Dec. 6, 1985 and now U.S. Pat. No. 4,797,285, and is based on the ability of the chelator/free-radical scavenger combination to inhibit both the initiation and propagation of free-radical reactions in a liposome suspension.

The lipophilic free radical scavenger used in the composition is preferably $\alpha$-T, or a pharmacologically acceptable analog or ester thereof, such as $\alpha$-T succinate. Other suitable free radical scavengers include butylated hydroxytoluene (BHT), propyl gallate (Augustin), and their pharmacologically acceptable salts and analogs. Additional lipophilic free radical quenchers which are acceptable for parenteral administration in humans, at an effective level in liposomes, may also be used. The free radical quencher is typically included in the lipid components used in preparing the liposomes, according to conventional procedures. Preferred concentrations of the protective compound are between about 0.2 and 2 mole percent of the total lipid components making up the liposomes.

The water soluble iron-specific chelating agent may be selected from the class of natural and synthetic trihydroxamic acids and characterized by a very high binding constant for ferric iron (on the order of $10^{30}$) and a relatively low binding constant for 2-valence cations, such as calcium and magnesium. A variety of trihydroxamic acids of natural origin are known, including compounds in the ferrichrome class, such as ferrichrome, ferrichrome A, and albomycin; compounds in the ferrioxamine class, including the ferrioxamines and ferriomycines; and compounds in the fusaramine class. Alternatively, the chelator may be a tetraacetic acid or pentaacetic acid chelator such as EOTA, DPTA, or ED3A.

The chelating agent is present in the composition at a concentration which is in molar excess of the ferric iron in the liposome suspension.

B. Liposome Preparation

The liposomes may be prepared by a variety of techniques, such as those detailed in Szoka et al. One preferred method for preparing drug-containing liposomes is the reverse phase evaporation method described in reference 3 and in U.S. Pat. No. 4,235,871. In this method, a solution of liposome-forming lipids is mixed with a smaller volume of an aqueous medium, and the mixture is dispersed to form a water-in-oil emulsion. The drug to be entrapped is added either to the lipid solution or aqueous medium. After removing the lipid solvent by evaporation, the resulting gel is converted to liposomes, with an encapsulation efficiency, for a water-soluble drug, of up to 50%. The reverse phase evaporation vesicles (REVs) have typical average sizes beween about 2-4 microns and are predominantly oligolamellar, that is, contain one or a few lipid bilayer shells. The oligolamellar nature of the vesicles may facilitate slow drug efflux and thus contribute to a lower efflux half life for an encapsulated drug. One advantage of REVs in the present invention is the high ratio of encapsulated drug to lipid which is possible, allowing greater drug doses to be administered by a surface coating of liposomes. Preparation of REVs is described in Example V.

A simple lipid-hydration procedure for producing multilamellar vesicles (MLVs) may be preferred where high drug encapsulation efficiency is not desired. In this procedure, a mixture of liposome-forming lipids dissolved in a suitable solvent is evaporated in a vessel to form a thin film, which is then covered by an aqueous solution of the drug. The lipid film hydrates to form MLVs, typically with sizes between about 0.1 to 10 microns. As in the REV method, the drug to be encapsulated is added either to the initial lipids or to the hydrating medium, depending on its solubility in water. The percent of total drug material which can be encapsulated in the MLVs, calculated as the ratio of encapsulated drug to total drug used in vesicle preparation, is typically between about 5-20% for water-soluble drugs. MLV preparation is also illustrated in Example V.

Either the REV or MLV preparations can be further treated to produce a suspension of smaller, relatively homogenous-size liposomes, in the 0.1-1.0 micron size range. Advantages of smaller, more homogeneous-size liposomes are: (1) more uniform drug release properties, (2) higher density of liposome packing allowed at a mucosal tissue surface, and (3) greater optical clarity in ophthalmic applications. One effective sizing method involves extruding an aqueous suspension of the liposomes through a polycarbonate membrane having a selected uniform pore size, typically 0.2, 0.4, 0.6, 0.8 or 1 microns (reference 3e. The pore size of the membrane corresponds roughly to the largest sizes of liposomes produced by extrusion through that membrane, particularly where the preparation is extruded two or more times through the same membrane. A more recent method involves extrusion through an asymmetric ceramic filter. The method is detailed in co-owned U.S. patent application for Lipsome Extrusion Method, Ser. No. 829,710, filed Feb. 13, 1986 and now U.S. Pat. No. 797,285.

Alternatively, the REV and MLV preparations can be treated to produce small unilamellar vesicles which are characterized by sizes in the 0.04-0.08 micron range. Because of the small particle sizes, SUV suspensions can be optically quite clear, and thus advantageous for ophthalmic applications. Another advantage of SUVs, as suggested above, is the greater packing density of liposomes on a mucosal surface which can be achieved with smaller liposome particles. This feature is valuable, for example, in one of the novel uses of the invention, where the liposomes are used as an ocular lubricant in the treatment of dry eye.

One preferred method for producing SUVs is by homogenizing an MLV preparation, using a conventional high pressure homogenizer of the type used commercially for milk homogenization. Here the MLV preparation is cycled through the homogenizer, with periodic sampling of particle sizes to determine when the MLVs have been substantially converted to SUVs. This method is illustrated in Example V, which describes the conversion of MLVs to SUVs with both moderate-pressure and high-pressure homogenization.

SUVs containing either 30 moles percent lysinyl PE or 30 mole percent cholesterol ester of $\beta$-alanine were examined for stability, as evidence by the leakage of encapsulated radiolabeled sucrose from the liposomes. REVs and MLVs would be expected to be even more stable for encapsulation, since leakage effects related to membrane curvature strain and unequal charge distribution across the membrane would be less.

After final sizing, the liposomes can be treated, if necessary, to removed free (non-entrapped) drug. Conventional separation techniques, such as centrifugation, diafiltration, and molecular-sieve chromatography are suitable.

The following examples illustrate specific methods for synthesizing amine-derivatized lipid components, and for producing liposomes with selected mucosal retention properties.

C. Liposome Binding to Mucosal Tissue

Several studies referred to above, and described in Examples VII-XI, demonstrates the enhanced binding of the liposomes of the invention to ocular tissue. It is likely that the enhanced retention of liposomes to mucosal epithelium involves electrostatic binding of the positively charged liposomes to mucin, a negatively charged glycoprotein which is produced by the goblet cells of the conjunctiva, and which remains bound to the epithelium. Since all other mucosal tissue types, including nasal, oral, vaginal, rectal, and gastrointestinal mucosa, are characterized by epithelial cells which produce a cell-bound mucin, it is expected that the liposomes of the invention would show enhanced retention to all mucosal tissue types. The studies reported in Examples XII verify that a significantly enhanced liposome retention is seen with a variety of other tissue types, including trachea, esophagus, stomach, small intestine, and rectum. The study compared the binding to the tissue of uncharged liposomes with liposomes containing either 20 mole percent stearylamine or 20 mole percent lysine lysinyl PE. As summarized in Table VI of Example XII, both positively charged liposome preparations showed enhanced adhesion to most of the mucosal tissue type compared to the adhesion of the neutral liposomes. Lys-lys-PE liposomes showed twice the percent adhsesion to the trachea, esophagus and small intestine and a lesser but significant enhanced adhesion to the stomach and rectum relative to the stearylamine containing liposomes.

III. Formulations and Uses

A. Liposome Suspensions

The aqueous liposome suspensions prepared as above are suited to ophthalmic uses in which the liposomes are applied in droplet form to the eye. For ophthalmic use, the liposomes are preferably sized, relatively small REVs or MLVs, or SUVs, typically at lipid concentrations of between about 5 and 50 $\mu$mole lipid/ml.

As indicated above, the retention of liposomes on mucosal tissue can be enhanced by including in the suspension, high molecular weight polymers which act to increase suspension viscosity. Typical polymers for use in ophthalmic formulations are methylcellulose, hydroxyethylcellulose, hydroxypropylcellulose, and polyvinylalcohol. The effect of these polymers on ocular retention wsa examined in the studies reported in Example XI. In a first study, SUVs prepared with either 20 mole lysinyl PE or lysine lysinyl PE were formulated in a dilute suspension of buffer alone or buffer containing 0.8% hydroxyethylcellulose and 0.2% polyvinylalcohol, and ocular retention over a 1 hour period was measured. As may be seen, addition of polymers (solid symbols) significantly increased the level of liposome retention after 1 hour in both lysinyl PE SUvs (circles) and in lysine lysinyl PE SUVs (triangles).

A second study examined the effect of the Neo-Tears ™ polymer (a product of Barnes Hind, Sunnyvale, CA) on retention of SUVs having a variety of lipid compositions. Interestingly, the polymers enhanced the retention of uncharged liposomes only slightly (closed squares vs open squares), in contrast to the effect seen in FIG. 6 for charged SUVs. The other data plots in FIG. 7 show retention of polymer solutions of SUVs containing different concentrations of lysinyl PE (circles) and lysine lysinyl PE (triangles).

In one general application, the liposomal formulation is used to produce a sustained drug release at the ocular tissue site. Ophthalmic drugs suitable for delivery in liposomal-entrapped form, for sustained release over a several-hour period, include: antiviral agents, such as fluorouracil, iodouridine, trifluorouridine, vidarabine, azidothymidine, ribavirin, phosphonoformate, phosphonoacetate, and acyclovir; anti-allergic agents such as cromolyn, cemetidine, naphazoline, lodoxomide, and phenylepinephrine; anti-inflammatory agents such as predisolone, dexamethasone, and supraphen; and anti-glaucoma agents which act by lowering intraocular pressure, such as carbacol, N-demethylcarbacol, pilocarpine, anti-glaucoma agents which act as cholinesterase inhibitors, such as isoflurophate, exothioiodate, and demecarium bromide, and anti-glaucoma agents which act as $\beta$-blockers, such as timolol, depaxolol, metipranalol, levobunalol, and celiprolol.

According to one advantage of the liposome suspension, the amount of drug which is delivered in drop form may be substantially higher than that allowable in free solution form, since undesired side effects related to high free drug concentrations are reduced.

The liposomes suspensions are also useful in ophthalmics for treating dry eye. This condition, which is characterized by poor moisture retention on the eye, has a number of distincy eitologies, including poor water-secretion by the lacrimal gland (Sjögren), poor mucin secretion by goblet cells (Lemp), vitamin A deficiency (Lawrence), and alteration of film-forming lipids as a result of chronic blepharitis. These are primarily long-chain alcohols and acids and cholesterol esters, which are required for forming a stable preocular tear film (Anderson).

Conventional dry eye formulations are polymer solutions which provide, when applied to drop form, a film of moisture which has increased retention on the eye by virtue of the solution viscosity. The liposome formulation of the present invention provides three important advantages over these earlier formulations. First, the liposomes in the suspension are retained on the eye in appreciable quantity for several hours, in contrast to viscous solutions which are largely cleared after 1 hour. Second, the surface-bound liposomes provide a matrix for holding encapsulated and bound aqueous fluid. Third, the liposomes themselves can be formulated to supply necessary lipids needed for film formation. Long-chain alcohols and fatty acids, and cholesterol esters which make up the films are all compatible with stable vesicular structures. Further, experiments conducted in support of the present invention indicated that the aqueous ocular environment contains phospholipases capable of deacylating phospholipids to yield long-chain fatty acids.

Several considerations are important in formulating a liposomal suspension for dry eye treatment. One preferred lipid composition contains lipid components designed to contribute to film forming on the eye surface. For example, the phospholipid components can be selected to yield optimal long chain fatty acids after hydrolysis. Small amounts of long chain alcohols after hydrolysis. Small amounts of long chain alcohols and fatty acids can also be included without destabilizing the liposomes appreciably.

Another important consideration, in the choice of lipid components, is to minimize the extent of oxidative lipid damage which can occur on storage, particularly where, as is usual, the formulation will be stored over a several month period at room temperature. Oxidative damage can be reduced, as discussed above in Section IIA, by using predominantly saturated phospholipids and cholesterol analogs (e.g., cholestanol), and actively inhibiting free-radical reactions by the combined action of a lipophilic free-radical scavenger, such as $\alpha$-tocopheral and a water-soluble iron-specific chelator, such as desferrioxamine.

It is also important to minimizing lipid hydrolysis which occurs on storage, and again particularly at room temperature or above. This problem has been examined in studies designed to measure the degree of phospholipid hydrolysis which is observed in a liposome/NeO-Tear ™ formulation adjusted to a pH of 6.0, 6.8, 7.4, or 8.0. Lipid hydrolysis at 70° C. was measured after 1, 2 and 5 days. The extent of hydrolysis observed after five days incubation ranged from less than 5% at pH 6.0, to nearly 30% at pH 8.0. Therefore, a pH close to pH 6.0, and preferably no greater than pH 6.5, minimizes this problem.

Still another consideration is achieving good optical clarity in a liposome/polymer suspensions. In addition to liposome size, which is discussed above, the liposomes and polymers must be stable in terms of aggregate effects, such that if aggregation occurs, the liposome/polymer complexes can be easily dispersed by shaking. For both of the hydroxyethylcellulose/polyvinylalcohol, and NEO-TEARS ™ polymers used in formulating ophthalmic liposomes, good optical clarity after two months storage at room temperature, and clouding which was observed could be cleared by moderate shaking.

B. Aerosolized Liposomes

Aerosolized liposomes, or liposome sprays are a convenient vehicle for applying the liposomes to the nasal or oral mucosa. In one simple embodiment, the liposomes are formulated as a dilute aqueous suspension, and sprayed from a conventional pump or squeeze spray bottle. In more elaborate embodiments, the liposomes are formulated for use with flurocarbon propellant solvents in a pressurized cannister system. Several liposome formulations which are suitable for use with propellant solvents are disclosed in co-owned U.S. Patent Application for "Lipsome Inhalation System and Method", Ser. No. 737,221, filed May 22, 1985 and now abandoned, and PCT Patent Application No. PCT/US86/01095 for "Lipsome Inhalation System and Method", filed May 22, 1986, which applications are incorporated by reference herein. Briefly, the liposomes may be suspended in the propellant in powdered or aqueous paste form, or combined in paste or powdered form with the propellant during propellant release from the pressurized cannister.

Exemplary drugs for delivery to the nasal mucosa in liposomal form include anti-allergens, anti-histimines, such as benzdryl, diphenhydramine HCl clemeastine fumarate, promethazine HCl, and tripolidine HCl; vasoconstrictors, such as metaraminolbitartrate, epinephrine, norepinephrine, phenylephrine HCl, and ephedrine; and peptide hormones, such as insulin, calcitonin, growth hormone, epidermal growth factor, atrial natriuretic peptide, vasopressin, and oxytocin.

Exemplary drugs for delivery to the oral mucosa include anesthetics, such as benzocaine, lidocaine HCl, dyclonine HCl; and antiviral or antibacterial agents, such as amantadine HCl, fluroruracil, iodouridine, gentamicin, erythromycin, cephalosporin, and tetracycline.

C. Liposome Paste and Foam Formulations

Paste or form formulations of the liposomes provide advantages of (1) relatively good stability on storage, (2) high drug capacity and (3) a high ratio of liposome-entrapped to free drug, particularly for water-soluble, liposome-permeable drugs. Liposome pastes or foams are suitable for application to burned or broken skin, ocular tissue, and in body cavities, where the high viscosity of the material helps maintain the material at the site of application.

Methods for generating liposome paste with up to 70% encapsulated aqueous volume have been described in co-owned patent application Ser. No. 860,528 for "Liposome Concentrate and Method", filed May 7, 1986 and now abandoned. The concentrate is preferably formed by ultrafiltration with continued recycling of the liposome suspension material.

Liposome foams can be prepared using conventional two-chamber propellant devices, such as are used for cosmetic foams, such as having shaving cream. Here a heavy liposome suspension contained in one chamber is mixed with propellant gas contained in a second chamber, and the gassified mixture of foam is expelled under the propellant release pressure through a discharge nozzle. U.S. Pat. No. 6,326,416 describes a two-chamber propellant foam device which could be adapted readily for use in liposome foam generation.

D. Solid Matrix Formulations

The high-retention liposomes of the invention can be embedded or encapsulated within several types of solid matrix supports, either to protect the liposomes from rapid clearance or breakdown and/or to provide slow release the liposomes from the matrix into the region of tissue mucosa. One type of matrix is a suppository designed either to be melted or dissolved in a body cavity, to release the embedded liposomes. Conventional materials and preparation methods for suppositories would be suitable, to the extent the liposomes are not exposed to transient temperatures above about 60 C.

Biocompatible polymers, such as collagen, polylysine, polylactic acid, polymethyacrylate, polyurethanes, polyglycolic acid, hydroxypropylcellulose, agar and agarose, are also suitable bulk carriers for the liposomes of the invention. Methods for preparing these polymers in cross-linked and/or gel form are well known, and the methods can be readily adapted to incorporate liposomes, again with the proviso that transient temperatures above about 60 C. are avoided. Many of the polymers, such as agar, collagen, and polyurethanes can be formulated in permeable cross-linked structures which allow liposome movement through and out of the matrices at a selected rate. Matrices of this type are suitable for drug delivery in body cavities, where the matrix can be held in place over an extended period, or for ocular use, where the implant can take the form of a clear lens or the like. Other polymer compositions, like polylactate, can be formulated as a biodegradable solid which release the entrapped slowly over an extended polymer degradation period. Such matrices are suitable for liposome release in the mouth or stomach. Some of the polymer compositions, such as polylysine, can be polymerized in a liposome suspension to form a polymer shell about individual liposomes, to form a coating which, for example, would protect the liposomes from rapid breakdown in the stomach.

From the foregoing, it can be appreciated how various objects and features are met. The liposomes of the invention give significantly enhanced binding to mucosal surface, by virtue of a high concentration of spaced positive charges on the liposomes surfaces. Additional enhancement is achieved in a close-packed lipid arrangement in the liposomes. The phospholipid, diglyceride, and cholesterol lipid moieties which anchor the positive charges to the liposome membrane are tightly bound and contribute generally to close-packing in the lipid bilayer. Unlike smaller single acyl chain components which have been proposed heretofore, the derivatized components of the present invention do not show toxicity effects at the relatively high concentrations needed to enhance binding to mucosal tissue.

The liposomes can be prepared to include a broad range of drugs or other pharmaceutical agents, such as vitamins, peptides, enzymes or enzyme cofactors and the like, which are usefully administered to mucosal tissue in sustained release form. In particular, the combination of liposomes, which provide slow release of the entrapped drugs, and long-term liposomal retention at the mucosal tissue site, allow an entrapped drug to be released in a sustained fashion over a several hour period, and at the same time, allow relatively high drug doses with reduced side effects associated with a high concentration of free drug.

In another therapeutic use, the enhanced-retention liposomes provide several advantages over polymer solutions for treating dry eye.

The liposomes can be formulated in a variety of drug-delivery vehicles, including suspensions, aerosols, pastes, and solid matrix vehicles for delivering the liposomes to mucosal tissue in an optimal manner.

The following examples illustrate methods for forming and using the enhanced-retention liposomes of the invention, and binding characteristics on ocular and other mucosal tissues.

MATERIALS

L-lysine, L-arginine, L-histidine, L-ornithine, L-lysinyl-lysine, and L-lysinyl-lysinyl-lysine were obtained in monohydrochloride form from Sigma Chem Co. (St. Louis, MO); di-tert-butyldicarbonate, from Aldrich Chemical Co. (Milwaukee, WI); dicyclohexylcarbodiimide (DCCI), from Aldrich Chemical Co. (Milwaukee, WI); egg phosphatidylethanolamine (egg PE) and egg phosphatidylcholine (egg PC), from Avanti Polar Lipids, Inc. (Birmingham, AL); cholesterol (greater than 99% pure), from Nu-Chek (Elysian, MN); cholesteryl iodide, from Sigma Chemical Co. (St. Louis, MO); glycine. B-alanine, 4-aminobutyric acid, 5-amino valeric acid, and 6-aminocaproic acid, from Sigma Chemical Co. (St. Louis, MO); N,N'-bis-(3aminopropyl)-piperazine, from Aldrich Chemical Co. (Milwaukee, WI); potassium phthalimide, from Aldrich Cem. Co (Milwaukee, WI); trinitrobenzenesulfonic acid (TNBS) from Aldrich Chemical Co. (Milwaukee, WI); silica gel TLC plates, from J. T. Baker Chem. Co. (Phillipsburg, NJ); Kieselgel 60, 70–230 mesh, from E.M. Science Company, (San Francisco, CA); alumina, 80–200 mesh, from Fisher Scientific (Springfield, NJ); aluminum-hydroxide coated TLC plates, from E. Merck (Daumstadt, Germany); celite 545, from J. T. Baker Chem. Co. (Phillipsburg, NJ); Bio-Gel A 40M agarose, from Bio-Rad (Richmond, CA); and Neo-Tears ™, from Barnes-Hines (Mt. View, CA).

EXAMPLE I

Preparation of Lysine-Derivatized PE

A. Preparation of tBOC-Lysine 1.83 g (10 mmole) of L-lysine were added to a solution of 20 ml of 1.0N sodium hydroxide in 20 ml dioxane. The mixture was stirred until the lysine hydrochloride completely dissolved, then cooled in an ide bath until the temperature fell to 5° C. To the resulting solution was added slowly 4.8 g (22 millimoles) di-tert-butyldicarbonate, keeping the temperature below 10° C. After ½ hour, the ice bath was removed and stirring continued for another ½ hour at room temperature.

The dioxane and much of the water were removed under vacuum, and the residue was taken up in 50 ml water. Aqueous $NaHSO_4$ was added to pH 2–3. The resulting di-tert-butoxycarbonyl-lysine (tBOC-lysine) was extracted into three successive 50 ml portions of ethyl acetate. The combined extracts were washed with 15 ml water, dried over anhydrous sodium sulfate, and evaporated under vacuum, yielding 4.01 g colorless oil. Thin layer chromatography (TLC) on silica gel coated plates, using $CHCl_3$, $CH_3OH$, $H_2O$, 65:25:4 (v/v) and visualized with ninhydrin, showed that the product consists largely of a single product with an $R_f=0.53$.

B. Preparation of the Anhydride of tBOC-Lysine 1.20 g (about 3 mmole) of crude tBOC-lysine from IA were dissolved in 15 ml chloroform and treated with 660 mg (3.2 mmole) of DCCI. Crystals of dicyclohexylurea began to separate after two to three minutes. The reaction mixture was subsequently permitted to stand at room temperature overnight.

The suspension was filtered with suction to remove the dicyclohexylurea, and the filter cake was washed with a few ml of chloroform. The washings were combined with the filtrate and used immediately in the preparation of the PE amide of tBOC-lysine.

TLC on silica gel coated plates, using $CHCl_3$, $CH_3OH$, $H_2$; 65:25:4 (v/v) and visualized with ninhydrin, showed a predominant spot with an $R_f=0.62$.

C. Preparation of the PE Amide of tBOC-Lysine

The entire chloroform solution (filtrate), containing no more than 1.5 mmole of the anhydride of tBOC-lysine, was added to 900 mg (1.21 mmole) of egg PE and 200 µl (1.43 mmole) of triethylamine. The solution was permitted to stand 18 hours at room temperature and then evaporated to constant weight under vacuum. The residue was redissolved in 10 ml chloroform and used directly in the preparation of the PE amide of lysine.

Thin-layer chromatography of the resulting solution in silica gel coated TLC plates, using $CHCl_3$, $CH_3OH$, $H_2O$, 65:25:4 (v/v), and visualized with ninhydrin, gave a predominant phosphorous-containing spot with an $R_f=0.60$.

D. Preparation of PE Amide of L-Lysine

The crude PE amide of tBOC-lysine prepared as in IC, containing at most 1.5 mmole product, was dissolved in 10 ml chloroform and then treated with 5 ml trifluoroacetic acid and 54 µl (3.0 mmole) of water. A few aluminum oxide boiling granules were added and the mixture was permitted to stand at 23° C. for one hour. During this time, gas was evolved.

The solvent was removed under vacuum and the residue redissolved in 35 ml chloroform and 35 ml ethyl acetate. Ten percent sodium carbonate was added until the pH reached 10. Phases were separated, using centrifugation if necessary, and the organic phase was washed with 5 ml water. Evaporation to constant weight under vacuum gave 1.30 g of crude L-lysine PE.

The crude L-lysine PE was dissolved in 10 ml chloroform and placed at the top of a 21 mm × 270 mm chromatographic adsorption column packed with Kieselgel 60, 70–230 mesh. Development was with 100 ml 5% methanol in chloroform, followed by 100 ml 10% methanol in chloroform, followed by 200 ml 20% methanol in chloroform, followed by 400 ml 100% methanol. Separate 50 ml aliquots of column effluent were saved and analyzed by TLC, using $CHCl_3$, $CH_3OH$, $H_2O$; 65:25:4. Those fractions containing only a ninhydrin positive, phosphate positive material which migrated with an $R_f=0.15$ to 0.17 were combined and evaporated under reduced pressure, yielding 350 mg of colorless wax. The desired PE product was in the early 100% methanol effluents.

The calculated and experimentally determined phosphate values for the PE amide product are 12.76% and 12.88%, respectively.

EXAMPLE II

Preparation of Arginine-Derivatized PE

A. Preparation of tBOC-arginine 174 mg (1.0 mmole) of L-arginine were suspended in 3 ml 2:1 dioxane:water, to which was then added 1 ml of 1.0N sodium hydroxide. The resulting clear solution was cooled in an ice bath and treated, with stirring, with 240 mg (1.1 mmole) of di-tert-butyl dicarbonate. After ½ hour, the ice bath was removed and stirring was continued for another hour at room temperature.

The dioxane was removed under vacuum and the residue taken up in 5 ml 1-butanol. To this was added an ice-cold solution of 138 mg (1.0 mmole) sodium hydrogen sulfate monohydrate in 1 ml water.

Separation of the 1-butanol phase, followed by vacuum evaporation yielded 290 mg of a colorless, friable solid, consisting largely of tBOC arginine.

B. Preparation of the PE Amide of t-BOC-Arginine

The entire 290 mg of crude tBOC-arginine from IIA was added to 150 mg of egg PE (0.20 mmole) dissolved in 7.5 ml chloroform. To the solution was next added 290 mg (1.41 mmole) DCCI and 168 µl (121 mmole) of triethylamine. The solution was subsequently evaporated to a volume of 0.8 ml under a dry stream of nitrogen and permitted to react overnight at room temperature.

TL chromatography on silica gel coated plates, using CHCl₃, CH₃OH, H₂O, 65:25:4 (v/v), gave a predominant phosphate-containing spot with $R_f=0.61$.

C. Preparation of L-Argininyl Egg PE

The chloroform solution of the egg PE amide of tBOC-arginine from IIB was diluted to 2.0 ml with chloroform and 0.7 ml trifluoracetic acid and 18 μl of water (1 mmole) and let stand at room temperature for 1 hour.

At the end of this time, 5 ml chloroform and a solution of 800 mg (7.55 mmole) anhydrous sodium carbonate in 5 ml water were added slowly and then shaken after carbon dioxide evolution had subsided. The phases were separated with centrifugation and the aqueous phase was reextracted twice with an equal volume of chloroform.

The combined chloroform extracts were dried over anhydrous sodium sulfate and placed at the top of a 10 mm×240 mm chromatographic absorption column packed with Kieselgel 60, 70–230 mesh.

The column was developed by passing through it, in sequence, 50 ml 100% chloroform, 50 ml 10% methanol in chloroform, 50 ml 20% methanol in chloroform, 50 ml 40% methanol in chloroform, and 100 ml 100% methanol. Twenty ml portions of effluent were saved and analyzed by TLC on silica gel coated plates, using CHCl₃, CH₃OH, H₂O, 65:25:4 (v/v) as developer. Those fractions which contained a phosphate positive and ninhydrin positive spot with $R_f$ about 0.17 were combined. Evaporation to dryness yielded about 9 mg of colorless waxy material.

The calculated and experimentally determined phosphate values for the PE amide product are 10.56% and 9.9%, respectively.

EXAMPLE III

Preparation of the Cholesterol Esters of Different Chain Length Amino Acids

This section describes the preparation of five cholesterol esters of different chain length amino acids. The five esters have the general formula shown below, and include the compounds n=1–5, i.e., in which the length of the spacer arm separating the cholesterol hydroxyl oxygen from the terminal amine group is 2–6 carbon atoms:

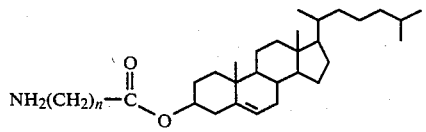

In general, the esters are formed by the steps of (A) N-protecting the corresponding amino acid, (B) forming the anhydride of the protected amino acid, (C) reacting the hydride with cholesterol, to form the corresponding cholesterol ester, and (D) deprotecting the ester to form the final product. Each of these steps will be illustrated below with respect to the synthesis of the cholesterol ester of 3-amino propionic acid (n=2). The reaction amounts and product characterization for all five compounds is given along with the specific details relating to the n=2 compound.

A. Preparation of tBOC-Amino-Propionic Acid

The amino acid protection reaction follows the general preparing tert-butoxycarbonyl amino acids described by Moroder, et al.

4.45 gm (50 mmole) of β-alanine were dissolved in a mixture of 50 ml 1N sodium hydroxide, 50 ml water, and 100 ml/dioxane. To the resulting solution cooled in an ice bath was added with stirring, at 10° C., 12.0 gm (55 mmole) of di-tert-butyl dicarbonate. When the reaction mixture temperature had fallen to 5° C., the ice bath was removed and stirring at room temperature was continued for another hour.

The solvents were removed under reduced pressure and the residue cooled in an ice bath. 10% aqueous sodium bi-sulfate was added until the pH fell to 2.5. The resultant oil was extracted into three successive 50 ml portions of ethyl acetate. The ethyl acetate extracts were combined, washed with 5 ml water, dried over anhydrous sodium sulfate, and evaporated to constant weight under vacuum.

The product, a pale yellow oil, eventually solidified yielding 7.35 gm of colorless crystals melting at 78°–79° C. The yield was about 78%. On TLC on SiO₂-coated plates, using CHCl₃, CH₃OH, H₂O; 65:25:4 as developer, and heated ninhydrin for visualization, the tBOC propionic acid appeared as a violet spot with $R_f=0.62$.

Table I below gives, for all n=1–5 compounds, corresponding molecular weights, amounts of starting material, yields, $R_f$ values on silica gel developed with CHCl₃:CH₃OH:H₂O (65:25:4) and color when heated in the presence of ninhydrin.

TABLE I

| n | 1 | 2 | 3 | 4 | 5 |
|---|---|---|---|---|---|
| mol. wt. | 75.05 | 89.09 | 103.1 | 117.2 | 131.2 |
| mg for 5 mmole | 375 | 445 | 516 | 586 | 656 |
| mg crude tBOC acid | 770 | 860 | 880 | 950 | 920 |
| $R_f$ | 0.50 | 0.62 | 0.66 | 0.71 | 0.78 |
| Color with ninhydrin | Pink-Brown | Violet | Purple | Mulberry | |

B. Preparation of the 3-tBOC-Amino-Propionic Acid Anhydride 7.35 gm (39 mmole) of t-BOC-propionic acid from III A were dissolved in 50 ml of chloroform. To the resulting solution was added 4.2 gm (20.36 mmole) of DCCI. Dicyclohexyl urea began to separate almost immediately.

After standing at 23° C. for two hours, the reaction mixture was filtered with suction to remove the by-product dicyclohexyl urea. The filter cake was washed with 10 ml chloroform and the washings were combined with the filtrate. Evaporation of the filtrate to dryness under reduced pressure gave 9.41 gm of colorless viscous oil.

When chromatographed on silica gel TLC plates, using CHCl₃, CH₃OH, H₂O, 65:25:4 as developer, and ninhydrin for visualization, the 3-tBOC-amino-propionic acid anhydride product appeared as a lilac spot with an $R_f=0.84$.

Table II below for all n=1–5 compounds, gives corresponding yields. $R_f$ values on silica gel developed with CHCl₃:CH₃OH:H₂O, 65:25:4, and color when heated in the presence of ninhydrin.

TABLE II

| | Anhydrides of W-tBOC-Amino Acids | | | | |
|---|---|---|---|---|---|
| | 1 | 2 | 3 | 4 | 5 |
| mg crude tBOC acid from 5 mmole | 770 | 860 | 880 | 950 | 920 |

TABLE II-continued

| | Anhydrides of W-tBOC-Amino Acids | | | | |
|---|---|---|---|---|---|
| | 1 | 2 | 3 | 4 | 5 |
| $R_f$ | 0.50 | 0.84 | 0.84 | 0.85 | 0.85 |
| Color with ninhydrin | Lilac | Lilac | Lilac | Lilac | Lilac |

C. The Cholesterol Ester of 3-tBOC-Amino Propionic Acid 9.41 gm (less than 19.5 mmole) of the crude anhydride from III B and 7.7 gm (19.9 mmole) of cholesterol and 20 ml pyridine were heated to 100° C. for six minutes, then permitted to cool spontaneously to room temperature.

Evaporation of the pyridine under vacuum yielded 22.2 gm of colorless crystals still smelling of pyridine, and consisting largely of the cholesterol ester of t-BOC-propionic acid.

Thin-layer chromatography of this product on silica gel coated TLC plates, using 50% cyclohexane-50% ethyl acetate as developer, and heating following a spray with 50% ethanolic sulfuric acid for visualization, gave a red spot at $R_f = 0.66$.

Table III gives the corresponding yields, $R_f$ values on silica gel developed with 1:n y cyclohexane: ethyl acetate 1:1, and color when heated in the presence of sulfuric acid.

TABLE III

| | tBOC Amino Acid Cholesterol Esters | | | | |
|---|---|---|---|---|---|
| n | 1 | 2 | 3 | 4 | 5 |
| mg crude product from 500 mg cholesterol | 1,620 | 1,528 | 1,467 | 1,577 | 1,468 |
| $R_f$ (SiO2, 50-50 cyclohexane ethyl acetate) | 0.67 | 0.66 | 0.66 | 0.61 | 0.58 |
| Color when heated @ $H_2SO_4$ | Red | Red | Red | Red | Red |

D. Preparation of the Cholesterol Ester of 3-Amino Propionic Acid 22.2 gm of crude cholesterol ester of 3-tBOC-amino propionic acid were dissolved in 20 ml chloroform. To this was added 20 ml trifluoracetic acid and 4 ml water, together with a few aluminum oxide boiling chips. The mixture was permitted to stand at 23° C. for 2 hours and then evaporated to dryness under vacuum, yielding 35 gm of syrup.

The syrup was redissolved in 100 ml chloroform and shaken with enough 10% aqueous sodium carbonate to raise the pH to 10. The resulting concentrate was suction-filtered through a filter coated with celite 545 to remove most of the suspended solid.

The chloroform was separated from the aqueous phase of the filtrate and the aqueous phase reextracted with 100 ml chloroform. The chloroform phases were combined, washed with 20 ml 10% $Na_2CO_3$, and evaporated to dryness to obtain 15.2 gm of a white paste.

Chromatography of the paste on a silica gel column was performed with successive washes of 100% chloroform, 5% methanol in chloroform, and 10% methanol in chloroform. The effluent fractions were assayed by TLC on $SiO_2$-coated plates, using $CHCl_3$, $CH_3OH$, $H_2O$, 65:25:4 as developer. The desired product appeared as a blue-green colored spot when sprayed with sulfuric acid and then gently heated. The $R_f$ is about 0.30. The chromatography column effluents containing only the desired products were combined and evaporated to dryness, yielding 7.0 gm of colorless oil which solidified at −20° C. The yield was 15.3 mmole, or about 77%, based on the amount of cholesterol added initially.

Table IV below gives the corresponding yields. $R_f$ values on silica gel when developed with $CHCl_3$: $CH_3OH$:$H_2O$ (65:25:4), and color when heated in the presence of either ninhydrin or $H_2SO_4$.

TABLE IV

| n | 1 | 2 | 3 | 4 | 5 |
|---|---|---|---|---|---|
| mg chromatographed product from 500 mg cholesterol | 240 | 493 | 137 | 151 | 194 |
| $R_f$ | 0.65 | 0.30 | 0.59 | 0.59 | 0.55 |
| Color with ninhydrin | Orange Yellow | Blue Green | Mulberry | Purple | Purple |
| Color with $H_2SO_4$ | Red | Red | Red | Red | Red |

EXAMPLE IV

Preparation of Epi-Cholesterol Amine Derivatives

A. Piperazine-Linked Cholesterol Amine

99.3 mg (0.20 mmole) of cholesteryl iodide and 400 mg (2.0 mmole) of N,N'-bis-(3-aminopropyl)-piperazine were added to 2.0 ml dimethylsulfoxide. The suspension was placed in an oil bath heated to 120° C. for 4 hours under a nitrogen atmosphere. After cooling to room temperature, two volumes of water were added and the mixture extracted into three successive double volumes of toluene. The toluene extracts were combined and evaporated to dryness to obtain 77 mg yellowish oil.

The entire yield of oil was placed at the top of a 10 mm×250 mm chromatographic adsorption column packed with alumina, 80-200 mesh. Development was with 50 ml 10% methanol in methylene chloride, followed by 50 ml 20% methanol in methylene chloride. Separate 10 ml aliquots of effluent were collected. The product was contained predominantly in the effluent containing 10% methanol in methylene chloride.

Evaporation to dryness under reduced pressure yielded 10.0 mg of the pale yellow waxlike product.

TLC on aluminum hydroxide coated plates, using $CHCl_3$, $CH_3OH$, $H_2O$, 65:25:4 (v/v) as developer, gave a product spot with $R_f = 0.20$. The spot absorbed $I_2$ vapor like a typical lipid and reacted with ninhydrin to produce a steel-grey color. With sulfuric acid, warmed, the spot produces a red color.

B. Epi-Cholesteryl Amine

198.6 mg (0.40 mmole) of cholesteryl iodide and 148.2 mg (0.80 mmole) potassium phthalimide were added to 2.0 ml dimethylsulfoxide. The mixture was heated to 100° C. for 1 hour under a blanket of dry nitrogen. After cooling to room temperature, an equal volume of water, together with enough 1 N hydrochloric acid to lower the pH to 3 or 4 was added. The mixture was extracted with eight successive 5 ml portions of toluene. The toluene extracts were combined and evaporated under reduced pressure, yielding 100 mg crude crystalline material.

To purify the N-epi-cholesterylphthalimide product, the product was taken up in 10 ml 1 N sodium hydroxide in methanol, heated under reflux for 4 hours, and taken up in 2 ml water. After extracting into methylene chloride and drying over anhydrous sodium sulfate, the resulting solution was placed on a 1 cm×25 cm chromatographic adsorption column packed with alumina, 80-200 mesh.

The chromatogram was developed successively with 50 ml methylene chloride, followed by 50 ml 5% methanol, followed by 50 ml 10% methanol in methylene chloride. Separate 20 ml portions of effluent were collected. Evaporation of the second portion of effluent collected yielded 10 mg of material still impure by TLC, on silica gel plates developed with 50% ethylacetate/50% cyclohexane.

Re-chromotography was developed successively with 50 ml methylene chloride, followed by 50 ml 5% methanol followed by 50 ml 10% methanol in methylene chloride. Separate 20 ml portions of effluent were collected. Evaporation of the second portion of effluent collected yielded 10 mg of material still impure by TLC, on silica gel plates developed with 50% ethylacetate - 50% cyclohexane.

Re-chromatography on $Al_2O_3$, using 50 ml 30°-60° petroleum ether, followed by 50 ml 50% petroleum ether and 50% methylene chloride, followed by 50 ml methylene chloride afforded a separation, gave the desired amine in the first sample eluted by 100% methylene chloride. Evaporation yielded 5 mg of colorless oil, essentially pure 5-cholestan-3-epi-amine.

TLC on silica gel plates, using 50% ethylacetate-50% cyclohexane as developer gave a single spot with $R_f=0.65$. Spraying the plate with sulfuric caused the spot to turn blue upon gentle warming.

EXAMPLE V

Preparation of REVs, MLVs and SUVs

This example describes the preparation of reverse phase evaporation vesicles (REVs), multilamellar vesicles (MLVs) and small unilamellar vesicles (SUVs) with a representative lipid composition containing 30 mole percent egg PC, 40 mole percent cholesterol, and 30 mole percent egg PE Amide of Lysine (Example I).

A. REVs

A total of 8 mg of the above lipid composition, containing 1 mole percent of α-tocopherol, was dissolved in 1 ml of diethyl ether. An aqeuios buffer containing 13 mM phosphate, 140 mM NaCl, pH 7.4 was added to the organic solvent to a final volume of 1.3 ml, and the mixture was emulsified by sonication for 1 minute, maintaining the temperature of the solution at or below room temperature. The ether solvent was removed under reduced pressure at room temperature, and the resulting gel was taken up in 1 ml of the above buffer, and shaken vigorously. The resultimg REV suspension had particle sizes, as determined by microscopic examination, of between about 0.1 to 20 microns, and the was composed predominantly of relatively large (greater than 1 micron) vesicles having one or only a few bilayer lamellae.

B. MLVs

A total of 93 g of the above lipid components with 1 mole percent alpha-tocopherol, were dissolved in 500 ml tertiary butanol. The dissolved lipid was freeze dried, then 1 liter of saline-buffer containing 13 mM phosphate, 140 mM NaCl, 0.02% EDTA, pH 7.4, was added to the lipid film. The MLVs formed on gentle shaking for two hours. Examination of the MLVs showed heterogeneous sizes between about 0.05 to 20 microns, and a predominance of multilayered structures.

B. SUVs

About 1 liter of the MLV suspension from above was cycled through a Gaulin Homogenizer, Model 15 M, (Everett, MA), at about 9000 psi, the optimum recommended operating pressure. Aliquots were withdrawn after numbers of cycles for analysis of particle size by dynamic laser particle sizing. The distribution of particle sizes was also examined by molecular sieve chromatography, using a 2% agarose gel (Bio—Gel A 40M) column. Profiles of lipid phosphorous eluting from the column reflect the transformation of large, multilamellar vesicles which are contained in the void volume, to small unilamellar vesicles which are included in the column and elute as a broad peak between about 0.08 and 0.04 microns.

As the lipid suspension was cycled through the homogenizer, the mean particle size of the vesicles progressively decreased. Based on the column elution profiles, about 60%, 75%, 87%, and 90% of the MLVs were converted to SUVs (less than about 0.06 microns) after 10, 20, 30, and 50 passages, respectively. The final preparation showed good optical clarity.

When the same MLV suspension was homogenized in a very-high pressure homogenizer (French Pressure Cell Homogenizer, Model J4-3338, SLM-Aminco, Urbana, IL), operated at a pressure of about 20,000 psi, smaller liposomes and better optical clarity were achieved. Column elution showed that only about 5% of the lipid vesicles were not completely converted from MLVs to SUVs.

EXAMPLE VI

Sucrose Release from Positively Charged Liposomes

REVs containing 30 mole percent PC, 40 mole percent cholesterol and 30 mole percent lysinyl PE (composition 1) or 70 mole percent PC and 30 mole percent cholesteryl B-alanile were prepared as in Example IV. The aqueous medium used in liposome preparation contained $^{14}C$ sucrose, yielding REVs with encapsulated $^{14}C$ sucrose. The vesicles were freed of free $^{14}C$ sucrose by washing with centrifugation.

The washed liposomes containing the entrapped sucrose were resuspended in a physiological saline-buffer, and incubated over a four hour period at room temperature. The amount of released sucrose was measured each hour over the incubation period. For both liposome compositions, the amount of free sucrose measured after 4 hour was about 10% of the total entrapped sucrose, indicating that the liposomes are quite stable for encapsulation of small molecular weight molecules.

EXAMPLE VII

Transbilayer Distribution of Lysinyl PE in SUVs

SUVs containing PC, and either 10 or 20 mole percent of PE, lysinyl PE or lysinyl-lysinyl PE were prepared as in Example V. A suspension of each SUV preparation was incubated with trinitrobenzenesulfonic acid (TNBS), a membrane-impermeable compound which reacts with amine groups to form a yellow color which cam be determined spectrophotometrically. By comparing the amount of color development in intact liposomes, versus the amount seen after exposure of the liposomes to Triton-X, a membrane-solubilizing agent, the percent of total amines which are present in the outer, accessible layer of the liposomes can be quantitated. The results, expressed as the mean and range (in parenthesis) of each preparation is seen in Table V below.

TABLE V

| PE Phospholipids | Concentration (moles %) | Surface Amino Reactive Groups |
| --- | --- | --- |
| PE | 10 | 58 (55-61) |
|  | 20 | 54 (53-56) |
| Lysinyl PE | 10 | 58 (54-62) |
|  | 20 | 76 (71-82) |
| Lysine Lysinyl PE | 10 | 76 (73-79) |
|  | 20 | 92 (89-95) |

As shown in Table V, about 58 and 54% of the amino groups appeared on the outer layer of the liposomes containing 10 and 20 mole % of PE respectively. These values correspond closely to a theoretical distribution of phospholipids between outer and inner monolayers (approximately 60 vs. 40%) for a single wall vesicle of 25 nm in diameter. Replacement of PE with 10 mole % of lysine PE (one net positive charge per molecule) resulted in a similar distribution of the amino groups (58% on external layer). Increasing the lysinyl PE concentration to 20 mole %, or by using 10 mole % of lysine lysinyl PE (two net positive charges per molecule), resulted in a much greater proportion of the amino groups exposed on the exterior surface (76%). In the cases of 20 mole % of lysine lysinyl PE about 92% of the amino groups were found on the exterior surface.

EXAMPLE VIII

Ocular Retention Effect of Surface Charge Concentration

Liposomes containing 40 mole percent cholesterol, either 10, 20, 30, or 40 mole percent lysinyl egg PE (from Example II), and remainder mole percent egg PC were prepared as in Example V. Control SUVs contained cholesterol and egg PC in a 40:60 mole ratio. All of the preparation contained about $10^5$ counts per minute (CPMs) of $^{125}$I-PE per 100 nmole lipid. The final concentration of the liposome preparations was about 10 umole lipids/ml.

In vivo ocular retention studies were performed in rabbit eyes using a scintillation probe technique. In each experiment, 10 μl of liposomes containing about 100 nmole lipids and $10^5$ cpm of $^{125}$I-labeled PE were applied to the rabbit eye. Retention was assessed with the gamma probe positioned over the eye. A constant distance between the probe and the eye of 2 cm was insured by fitting the probe into a plexiglas sleeve-holder. A ⅛ inch thick lead partition placed against the lacrimal-nasal region of the rabbit effectively blocked radioactive material which drained into the nasolacrimal region. Retention time was monitored over a period of 1 hour unless specified otherwise. From the chart recordings, peak height readings were obtained. Total radioactivity of each reading was calculated from a standard curve by in vitro measurements of standard dilutions of the radioactive liposomes. Percent retention was calculated based on counts per minute (CPM) of the original 10 μl sample.

The percent retention was measured at 2, 5, 10, 15, 30, 30, 45, and 60 minutes. Retention times of the five SUV preparations are shown in FIG. 1. All values represent the mean of four rabbit eye measurements. As seen from the figure PC SUVs (solid squares) are poorly retained, falling to less than about 5% within one hour. The PE lysinyl SUVs show increasing levels of lysinyl PE, on progressing from 10 mole percent (open circles), to 20 mole percent (open triangles), to 30 mole percent (open squares) to 40 mole percent (closed circles), where 1 hour retention is about 45% of the originally applied CPMs.

The retention of the 40 mole percent lysinyl PE liposomes was similarly measured at every hour over a five hour period. The data show a gradual drop in liposome counts to about 20 percent within three hours, and thereafter, a very gradual loss to slightly below 20% between hours 3 and 5.

In a second study, the effect on ocular retention of increasing amounts of lysinyl-lysinyl PE in SUVs was investigated. The four SUV preparation studies contained 40 mole percent cholesteryl, 10, 20, or 30 mole percent lysinyl-lysinyl PE, and remainder amounts of egg PC. A control, containing cholesterol and egg PE in a 40:60 mole ratio, was the same as above. The study was performed as above, by applying 100 μl of liposomes (about 100 nmoles) to the rabbit eye, and measuring the remaining counts with a gamma counter at five-minute intervals after administration. The results are shown in FIG. 2, where the control is indicated by solid squares, and SUVs with 10, 20, and 30 mole percent lysinyl-lysinyl PE, by open circles, closed triangle, and open squares, respectively. Consistent with the above results, increasing amounts of the doubly charged PE gave increasing retention. In general, and particularly for the 20 mole percent doubly-charged liposomes, the retention times are significantly higher than for the corresponding concentrations of singly charged PE SUVs.

EXAMPLE IX

Ocular Retention-Effect of Cholesterol

Four SUV preparations containing either lysinyl PE with or without cholesterol or lysine lysinyl PE with or without cholesterol were tested for ocular retention. The compositions were: (1) egg PC:lynsinyl PE, 80:20, (2) egg PC:lysinyl PE:cholesterol 40:20:40, (3) egg PC:lysine lynsinyl PE, 80:20, and (4) egg PC:lysine lysinyl PE:cholesterol 40:20:40. The SUVs were prepared as in Example V, and tested for ocular retention as in Example VIII.

The results are shown in FIG. 5. The solid circles, indicating cholesterol-free SUVs with lysinyl and lysine lysinyl PE, respectively, give about 10% and 20% retention, respectively, after 1 hour. Addition of 40 mole percent cholesterol to the lysinyl PE (open circles) or lysine lysinyl PE (open triangles) produced in both cases, about a 2.5 fold increase in ocular retention after one hour.

EXAMPLE X

Effect of Cholesterol/Amine Spacer Arm Length

Four SUV preparations containing 30 mole percent egg PC, 40 mole percent egg PE and 30 mole percent of (a) cholesteryl ester of glycine, (b) cholesteryl ester of B-alanine, (c) cholesteryl ester of ε-amino caproic acid, and (d) cholesterol (control) were prepared. With reference to the cholesteryl ester structure shown in Example III, compositions (a), (b), and (c) have n values 1, 2, and 22 3, respectively. The compositions were prepared as in Example V and tested for ocular retention as in Example VIII.

Figure 4:
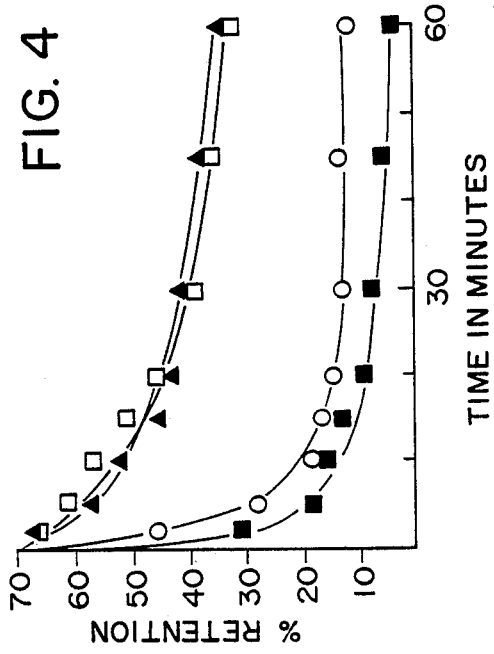
FIG. 4 shows the retention on an ocular tissue of liposomes prepared with various cholesterol ester amines, including a cholesterol control (solid squares), and the cholesterol esters of glycine (open circles), β-alanine (closed triangles), and ε-amino caproic acid (open squares).

The results are shown in FIG. 4. As seen the glycine ester gave only slightly enhanced retention over control SUVs (closed squares). By contrast both the B-alanine and ε-amino caproic esters gave retention values after 1 hour of about 40%, comparable to the enhanced retention seen in FIGS. 1 and 3 for SUVs with underivatized cholesterol and lysine derivatized PE components.

Figure 3:
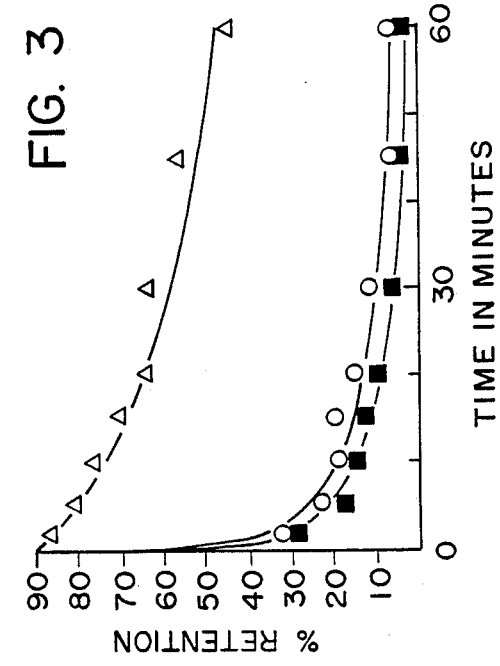
FIG. 3 shows the retention on an ocular tissue of liposomes prepared with various epi-cholesteryl derivatives, including a cholesterol control (solid squares), cholesterylamine (open circles): and cholesterylpiperazine (open triangles)

In a second test, SUVs containing 80 mole percent PC and either (a) 20 mole percent cholesterylamine (Example III), (b) 20 mole percent cholesteryl piperazine (Example III), or (c) cholesterol were prepared as in Example V. Ocular retention of the three preparations was determined as above. The results, seen in FIG. 3, show that the cholesterol piperazine component (open triangles) produces at least about a ten fold increase in retention after one hour, over the control (solid squares), cholesterol SUVs, but that cholesterylamine (open circles) produces only a slight enhancement.

EXAMPLE XI

Ocular Retention-Effect of Polymer Additives

In a first study, SUVs containing egg PC: lysinyl PE, 80:20 were mixed with equal volumes of either phosphate buffer (control) or a polymer solution containing 0.8% hydroxyethylcellulose and 0.2% polyvinylalcohol. Both compositions showed about 20% retention of labelled lipid counts after 1 hour, showing that the polymers produce very little improvement in ocular retention in non-cholesterol SUVs.

In a second study, SUVS composed of 40 mole percent egg PC, 40 mole percent cholesterol, and 20 mole percent of either lysinyl PE or lysine lysinyl PE were mixed with either the phosphate buffer of the polymer solution. All four preparations were tested for ocular retention as in Example VIII. The results are shown in FIG. 6. The lowest retention was seen for the control lysinyl PE SUVs (solid circles). Addition of polymer solution to the lysinyl PE SUVs (open circles) increased retention time nearly twofold after 1 hour. The control lysine lysinyl PE SUVs (closed triangles) gave substantially higher retention than either of the lysine PE preparations, and retention was enhanced still further by the presence of the polymer. A comparison of the the two studies indicate that (a) polymers can enhance the ocular binding of amine-derivatized liposomes, and (b) the enhancement requires the presence of cholesterol in the liposomes.

A third study examined the effects of Neo-Tears TM, a commercial ocular polymer solution on ocular retention of SUVs containing either lysinyl PE (20 or 30 mole percent) or lysine lysinyl PE (10 or 20 mole percent). A control preparation contained 20 mole percent PE. The SUVs all contained 40 mole percent cholesterol and remainder egg PC. The polymer solution was mixed with an equal volume of each SUV preparation.

The ocular retention over a 1 hour period of the polymer/SUV preparations is shown in FIG. 7. The two low-retention curves are for control SUVs with (solid squares) and without (open squares) the polymer. Thus the polymer provides some improvement, even in the absence of charge effects. The two lysinyl PE SUVs gave the retention plots indicated by the open and closed circles (20 and 30 mole percent lysinyl PE, respectively). The two lysine lysinyl PE SUVs gave the retention plots indicated by the open and closed triangles (10 and 20 mole percent lysine lysinyl PE, respectively). A comparison of the retention values for the lysinyl and lysine lysinyl SUVs in Neo-Tears vs no added polymer (FIG. 1 and 2) indicates that the polymer solution enhances retention of amine-derivatized SUVs.

EXAMPLE XII

Adhesion to Mucosal Tissues

This section compares the binding of lysine lysinyl PE SUVs to a variety of mucosal tissues. The retention of the lysine-lysinyl-derivatized SUVs is compared with that of uncharged SUVs, and with SUVs containing stearylamine. Earlier independent studies have shown that stearylamine containing SUVs gave only slight enhanced ocular binding over control, uncharged SUVs. The three SUV preparations were (a) PC:cholesterol:a-T (59:40:1); (b) PC:stearylamine:a-T (39:20:40:1); and (c) PC:lysine lysinyl PE:cholesterol (39:20:40:1). The three preparations each contained about the same specific activity of $^{125}$-I PE, as a radioactive marker.

A. Tissue Preparation Procedure

Female Sprague Dawley rats weighing 250 to 300 g were used. The esophagus, trachea, stomach, small intestine, and the rectum of the large intestine were dissected. The tissues were washed in Eagle's Basal Medium (BME) supplemented with penicillin and streptomycin, 1% fetal calf serum and 10 mm Hepes buffer. Cylindrical tissues were opened into rectangular pieces.

B. Tissue Adherence Test

The tissue pieces were placed on gauze pads and 20 $\mu$l of $^{125}$I-PE-liposomes samples were spread onto the lumen side such that none of the sample was in contact with the back side of the tissue. After one minute to several minutes, the samples were siphoned off and BME medium was used to rinse the mucosal tissue once. The wash medium was removed by siphon and the tissue was gently picked up by fine forceps and washed 3 times in 6 ml each of BME supplemented as described above. The tissue piece was then counted for $^{125}$I. After counting, the tissue piece was blotted dry and weighed. The $^{125}$I counts were then normalized to 100 mg tissue weight for comparison within each tissue type. At least 3 pieces of similar tissues were used to determine the adhesivity.

C. Incubation Time

Using the small intestine as the model, the minimal incubation time of the test liposomes were determined. Triplicate samples of the small intestine were used and the adherence of the lysine lysinyl-PE SUVs was tested, as described above, at room temperature. Total liposome sample used was 13,000 cpm/20 $\mu$l. The results are shown in Table V.

TABLE V

| Incubation Time Minutes | Average Adherent Radioactivity ± S.D. (cpm/mg Tissue Wt.) | % Adhesion ± S.D. |
|---|---|---|
| 1 | 3760 ± 257 | 28.9 ± 6.8 |
| 2 | 2155 ± 822 | 16.6 ± 38.2 |
| 5 | 3065 ± 629 | 23.6 ± 20.5 |
| 10 | 2154 ± 369 | 16.5 ± 17.1 |

The data showed that one minute incubation was sufficient to determine adherence in vitro. Longer incubation time gave a lesser degree of adherence and more variation probably due to partial digestion of the liposomes at the mucosal surface. Shorter incubation time was not tested because difficulty in handling shorter incubation times.

D. Adhesion of Liposomes to Different Mucosal Studies

Approximately equal concentration of lipid and radioactive counts of neutral, stearylamine liposomes and lys-lys-PE liposomes were incubated with the trachea, esophagus, stomach, small intestine and rectum tissue samples. The relative % adhesion were presented in Table VI.

TABLE VI

| Tissue | PC/C/αT | PC/C/SA/αT | PC/C/LysLysPE/αT |
|---|---|---|---|
| Trachea (n = 3) | 2.1 ± 0.8 | 6.6 ± 2.9 | 13.6 ± 4.1 |
| Esophagus (n = 5) | 2.2 ± 0.4 | 21.4 ± 7.3 | 38.4 ± 10.1 |
| Stomach (n = 4) | 1.2 ± 0.6 | 3.2 ± 1.9 | 5.2 ± 0.6 |
| Small Intest. (n = 5) | 7.7 ± 4.2 | 6.1 ± 2.4 | 14.0 ± 4.4 |
| Rectum (n = 3) | 2.3 ± 1.8 | 6.1 ± 3.3 | 8.5 ± 1.0 |
| 100% dose: | 28,580 cpm | 25,380 cpm | 27,230 cpm |

Both positively charged liposome preparations showed enhanced adhesion to most of the mucosal tissue types compared to the adhesion of the neutral liposomes. Lys-lys-PE liposomes showed twice the percent adhesion to the trachea, esophagus and small intestine and a significantly less enhanced adhesion to the stomach and rectum relative to the stearylamine containing liposomes.

While preferred uses and methods for carrying out the invention have been described herein, it will be apparent that various changes and modifications can be made without departing from the invention.

It is claimed:

1. A method for enhancing the binding of liposomes to a mucosal surface which comprises
    formulating the liposomes to contain and outer lipid layer containing between about 40–80 mole percent of neutral vesicle-forming lipids and between about 20–60 mole percent of positively charged vesicle-forming lipid component(s) selected from the group consisting of (a) dialiphatic lipid derivatives having (i) 2 aliphatic chains carried on a 3–4 carbon backbone, (ii) a polar atom attached to the backbone at a carbon atom which does not carry an aliphatic chain, (iii) an amine linked to the polar atom through a spacer at least 3 atoms long, and (iv) a net positive charge and (b) an amine-derivatized cholesterol having an amine group linked to the 6-membered cholesterol A ring by a carbon-containing spacer arm at least three atoms long, and
    including in the liposomes, a total amount of cholesterol, in the form of free cholesterol or said amine-linked cholesterol derivative, of between about 20–50 mole percent.

2. The method of claim 1, wherein the positively charged lipid component is a derivatized phospholipid of the form:

$$PE-N-\overset{H}{\underset{|}{C}}-\overset{O}{\underset{\|}{}}-Y-NH_2,$$

where $PE-NH_2$ is phosphatidylethanolamine, and $CO_2-Y-NH_2$ is a basic amino acid, or peptide containing a basic amino acid.

3. The method of claim 2, wherein the basic amino acid or peptide is selected from the group consisting of lysine, arginine, histidine, ornithine, and a peptide containing one of these basic amino acids.

4. The method of claim 1, wherein the derivatized cholesterol has the form:

$$Ch-O-C-Y-NH_2,$$

where Ch—OH is cholesterol and Y is a carbon-containing chain at least 2 atoms in length.

5. The method of claim 1, wherein the derivatized cholesterol has the form:

$$Ch-NH-Y-NH_2,$$

where $Ch-NH_2$ is cholesterol-3-amine, and Y is a carbon-containing chain at least two atoms long.

6. The method of claim 1, wherein the amine-derivatized lipid component(s) are predominantly amine-derivatized phospholipids, and the liposomes contain 25–45% cholesterol.

7. The method of claim 1, for use in enhancing the binding of the liposomes to an ocular surface, wherein the liposomes are contained in a suspension of high molecular weight polymer at a polymer concentration which increases the viscosity of the suspension.

8. The method of claim 1, for use in treating dry eye, wherein the phospholipid components in the liposomes are predominantly saturated in acyl chain moities, and which further includes applying the liposomes to the corneal surface of the eye.

9. The method of claim 8, wherein the liposomes are formulated to contain lipids selected from the group consisting of cholesterol esters and long-chain fatty alcohols.

10. The method of claim 8, wherein the liposomes are contained in a suspension medium containing polymers selected from the group consisting of hydroxyethylcellulose, hydroxypropylcellulose, methylcellulose, polyvinyl pyrrolidone, and polyvinylalcohol.

* * * * *

UNITED STATES PATENT AND TRADEMARK OFFICE
CERTIFICATE OF CORRECTION

PATENT NO. : 4,839,175

DATED : June 13, 1989

INVENTOR(S) : Guo, Luke; Redemann, Carl T.; Radhakrishnan, R.; Yau-Young, Annie.

It is certified that error appears in the above-identified patent and that said Letters Patent is hereby corrected as shown below:

In the Background:

Column 1, line 59, change "durg" to --drug--.

Column 1, line 62, change "adiministration" to --administration.

Column 1, line 65, change "soulution" to --solution--.

Column 1, line 65, change "majon" to --major--.

Column 2, line 1, change "drugs" to --drug--.

In The Background of the Invention:

Column 3, line 49, change "liposome" to --liposomes--.

Column 3, line 62, change "anhydried" to --anhydride--.

Column 4, line 8, change "aine" to --amine--.

In the Detailed Description of the Invention:

Column 9, line 32, change "n-1-5" to --n=1-5--.

Column 13, line 58, change "797,285" to --4,797,285--.

Column 14, line 56, change "adhsesion" to --adhesion--.

Column 15, line 8, change "wsa" to --was--.

Column 15, line 54, change "distincy" to --distinct--.

Column 15, line 54, change "eitologies" to --etiologies--.

Column 17, line 15, change "clemeastine" to --clemastine--.

Column 17, line 51, change "6,326,416" to --3,326,416--.

UNITED STATES PATENT AND TRADEMARK OFFICE
CERTIFICATE OF CORRECTION

PATENT NO. : 4,839,175

DATED : June 13, 1989

INVENTOR(S) : Luke S.S. Guo et al

It is certified that error appears in the above-identified patent and that said Letters Patent is hereby corrected as shown below:

In Example IX:
Column 28, line 43, add --and triangles-- after "circles".

In Example X:
Column 28, line 62, change "and 22 3," to --and >3,--.

Signed and Sealed this

Third Day of April, 1990

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,839,175                                  Page 1 of 2

DATED     : June 13, 1989

INVENTOR(S) : Guo, Luke; Redemann, Carl T.; Radhakrishnan, R.; Yau-Young, Annie.

It is certified that error appears in the above-identified patent and that said Letters Patent is hereby corrected as shown below:

In the Background:

Column 1, line 59, change "durg" to --drug--.

Column 1, line 62, change "adiministration" to --administration--.

Column 1, line 65, change "soulution" to --solution--.

Column 1, line 65, change "majon" to --major--.

Column 2, line 1, change "drugs" to --drug--.

In The Background of the Invention:

Column 3, line 49, change "liposome" to --liposomes--.

Column 3, line 62, change "anhydried" to --anhydride--.

Column 4, line 8, change "aine" to --amine--.

In the Detailed Description of the Invention:

Column 9, line 32, change "n-1-5" to --n=1-5--.

Column 13, line 58, change "797,285" to --4,797,285--.

Column 14, line 56, change "adhsesion" to --adhesion--.

Column 15, line 8, change "wsa" to --was--.

Column 15, line 54, change "distincy" to --distinct--.

Column 15, line 54, change "eitologies" to --etiologies--.

Column 17, line 15, change "clemeastine" to --clemastine--.

Column 17, line 51, change "6,326,416" to --3,326,416--.

UNITED STATES PATENT AND TRADEMARK OFFICE
CERTIFICATE OF CORRECTION

PATENT NO. : 4,839,175  
DATED : June 13, 1989  
INVENTOR(S) : Luke S.S. Guo et al It is certified that error appears in the above-identified patent and that said Letters Patent is hereby corrected as shown below:

In Example IX:
Column 28, line 43, add --and triangles-- after "circles".

In Example X:
Column 28, line 62, change "and 22 3," to --and >3,--.

Signed and Sealed this

Tenth Day of April, 1990

Attest:

HARRY F. MANBECK, JR.

*Attesting Officer*  *Commissioner of Patents and Trademarks*